(12) United States Patent
Alkhatib

(10) Patent No.: US 11,013,596 B2
(45) Date of Patent: *May 25, 2021

(54) TWO-STAGE COLLAPSIBLE/EXPANDABLE PROSTHETIC HEART VALVES AND ANCHORING SYSTEMS

(71) Applicant: St. Jude Medical, LLC, Abbott Park, IL (US)

(72) Inventor: Yousef F. Alkhatib, Edina, MN (US)

(73) Assignee: St. Jude Medical, LLC, Abbott Park, IL (US)

(*) Notice: Subject to any disclaimer, the term of this patent is extended or adjusted under 35 U.S.C. 154(b) by 67 days.

This patent is subject to a terminal disclaimer.

(21) Appl. No.: 16/384,141

(22) Filed: Apr. 15, 2019

(65) Prior Publication Data
US 2019/0240007 A1    Aug. 8, 2019

Related U.S. Application Data

(63) Continuation of application No. 15/466,182, filed on Mar. 22, 2017, now Pat. No. 10,299,919, which is a continuation of application No. 14/514,922, filed on Oct. 15, 2014, now Pat. No. 9,603,705, which is a continuation of application No. 13/886,851, filed on May 3, 2013, now Pat. No. 8,961,595, which is a continuation of application No. 12/733,758, filed as
(Continued)

(51) Int. Cl.
*A61F 2/24* (2006.01)

(52) U.S. Cl.
CPC .......... *A61F 2/2418* (2013.01); *A61F 2/2403* (2013.01); *A61F 2/2433* (2013.01); *A61F 2210/0014* (2013.01); *A61F 2220/0016* (2013.01); *A61F 2230/0054* (2013.01); *A61F 2230/0076* (2013.01); *A61F 2250/006* (2013.01); *A61F 2250/0069* (2013.01)

(58) Field of Classification Search
CPC .......... A61F 2/24; A61F 2/2412; A61F 2/2418
USPC ................................................. 623/2.1–2.19
See application file for complete search history.

(56) References Cited

U.S. PATENT DOCUMENTS

| 4,687,483 A | 8/1987 | Fisher et al. |
| 6,334,873 B1 | 1/2002 | Lane et al. |

(Continued)

FOREIGN PATENT DOCUMENTS

WO    2006127756 A2    11/2006

OTHER PUBLICATIONS

International Search Report for Application No. PCT/US2008/011077 dated Feb. 11, 2009.

*Primary Examiner* — Suzette J Gherbi
(74) *Attorney, Agent, or Firm* — Lerner, David, Littenberg, Krumholz & Mentlik, LLP

(57) ABSTRACT

Prosthetic heart valve apparatus is adapted for delivery into a patient in a circumferentially collapsed condition, followed by circumferential re-expansion at the implant site in the patient. The apparatus includes an annular anchoring structure that can be implanted in the patient first. The apparatus further includes an annular valve support structure, which supports a flexible leaflet structure of the valve. The support and leaflet structures are initially separate from the anchoring structure, but they can be implanted in the patient by interengagement of the support structure with the already-implanted anchoring structure.

16 Claims, 26 Drawing Sheets

Related U.S. Application Data application No. PCT/US2008/011177 on Sep. 26, 2008, now Pat. No. 8,454,686.

(60) Provisional application No. 60/995,812, filed on Sep. 28, 2007.

(56) References Cited

U.S. PATENT DOCUMENTS

| | | | |
|---|---|---|---|
| 7,951,197 B2 | 5/2011 | Lane et al. | |
| 8,454,686 B2 * | 6/2013 | Alkhatib | A61F 2/2403 |
| | | | 623/2.18 |
| 8,728,154 B2 * | 5/2014 | Alkhatib | A61F 2/2418 |
| | | | 623/2.17 |
| 8,784,481 B2 * | 7/2014 | Alkhatib | A61F 2/2418 |
| | | | 623/2.18 |
| 8,961,595 B2 * | 2/2015 | Alkhatib | A61F 2/2418 |
| | | | 623/2.18 |
| 9,572,660 B2 * | 2/2017 | Braido | A61L 27/54 |
| 9,603,705 B2 * | 3/2017 | Alkhatib | A61F 2/2433 |
| 9,615,921 B2 * | 4/2017 | Alkhatib | A61F 2/2409 |
| 10,299,919 B2 * | 5/2019 | Alkhatib | A61F 2/2418 |
| 2002/0032481 A1 | 3/2002 | Gabbay | |
| 2002/0099439 A1 | 7/2002 | Schwartz et al. | |
| 2002/0183840 A1 | 12/2002 | Lapeyre et al. | |
| 2003/0149477 A1 * | 8/2003 | Gabbay | A61F 2/2436 |
| | | | 623/2.14 |
| 2004/0186563 A1 | 9/2004 | Lobbi | |
| 2004/0193261 A1 | 9/2004 | Berreklouw | |
| 2004/0236411 A1 | 11/2004 | Sarac et al. | |
| 2005/0043790 A1 * | 2/2005 | Seguin | A61F 2/2403 |
| | | | 623/2.18 |
| 2005/0075725 A1 | 4/2005 | Rowe | |
| 2006/0142848 A1 | 6/2006 | Gabbay | |
| 2006/0190074 A1 | 8/2006 | Hill et al. | |
| 2006/0287719 A1 * | 12/2006 | Rowe | A61F 2/90 |
| | | | 623/2.18 |
| 2007/0100435 A1 * | 5/2007 | Case | A61F 2/2475 |
| | | | 623/1.24 |
| 2008/0071368 A1 | 3/2008 | Tuval et al. | |
| 2008/0133003 A1 | 6/2008 | Seguin et al. | |
| 2008/0140189 A1 | 6/2008 | Nguyen et al. | |
| 2008/0161911 A1 | 7/2008 | Revuelta et al. | |
| 2008/0188929 A1 * | 8/2008 | Schreck | A61F 2/2427 |
| | | | 623/2.38 |
| 2008/0215143 A1 * | 9/2008 | Seguin | A61F 2/2418 |
| | | | 623/2.17 |
| 2008/0228263 A1 * | 9/2008 | Ryan | A61F 2/2418 |
| | | | 623/2.11 |
| 2008/0249619 A1 | 10/2008 | Stacchino et al. | |
| 2009/0005863 A1 | 1/2009 | Goetz et al. | |
| 2009/0082858 A1 | 3/2009 | Nugent et al. | |
| 2010/0168839 A1 | 7/2010 | Braido et al. | |
| 2011/0112632 A1 | 5/2011 | Chau et al. | |
| 2011/0301692 A1 | 12/2011 | Seguin | |

* cited by examiner

TWO-STAGE COLLAPSIBLE/EXPANDABLE PROSTHETIC HEART VALVES AND ANCHORING SYSTEMS

This application is a continuation of U.S. patent application Ser. No. 15/466,182, filed Mar. 22, 2017, which is a continuation of U.S. Patent Application Ser. No. 14/514,922, filed Oct. 15, 2014, now U.S. Pat. No. 9,603,705, which is a continuation of U.S. Patent Application Ser. No. 13/886,851, filed May 3, 2013, now U.S. Pat. No. 8,961,595, which is a continuation of U.S. Patent Application Ser. No. 12/733,758, filed on Mar. 18, 2010, now U.S. Pat. No. 8,454,686, which is a national phase entry under 35 U.S.C. § 371 of International Application No. PCT/US2008/011177, filed Sep. 26, 2008, which claims the benefit of the filing date of U.S. Provisional Patent Application No. 60/995,812, filed Sep. 28, 2007, the disclosures of which are hereby incorporated by reference herein in their entireties.

BACKGROUND OF THE INVENTION

This invention relates to collapsible prosthetic heart valves and valve anchoring systems for use in less invasive approaches to heart valve replacement (or at least effective replacement).

Prosthetic heart valves are known that can be circumferentially collapsed for delivery into a patient via means that are less invasive than full open-chest, open-heart surgery. When such a valve reaches the implant site in the patient, the valve circumferentially re-expands and becomes an operating valve implant in the patient.

A prosthetic valve of the type described above may need to include a number of concentric layers of material and structure. For example, such a valve typically includes flexible leaflets inside an annular frame structure. Additional layers of material may be needed for such purposes as buffering (protecting) the leaflets from excessive contact with the frame structure and/or promoting ingrowth of tissue from the patient's surrounding body tissue structures. The frame structure must be strong enough to securely hold the prosthetic valve in place at the implant site in the patient.

The above requirements for a strong structure and a structure that includes several concentric layers of material can be inconsistent with the desire to circumferentially collapse the prosthetic valve to a relatively small diameter for less invasive delivery into the patient.

BRIEF SUMMARY OF THE INVENTION

In accordance with certain possible aspects of the invention, a prosthetic heart valve system may be deployed into a patient in two sequential steps. The system includes a collapsible/expandable anchoring platform (frame) and a collapsible/expandable valve with integrated leaflets (tissue, polymer, or other appropriate materials).

The system works by delivering and deploying (implanting) the anchoring platform first to provide a landing site for the collapsible/expandable valve, which is delivered next. The valve and anchoring platform have interlocking features that facilitate securement of the valve to the already-implanted anchoring platform. The anchoring platform also has features to secure itself to the native anatomy. There are several advantages to this approach that will be described later in this specification.

One of the desired features for minimally invasive (e.g., percutaneous, transapical, transseptal) approaches is low profile (i.e., relatively small diameter or circumferential size) of the valve/delivery system. Many have attempted to reduce this profile. However, this may result in trade-offs with respect to valve performance. With the two-step approach of this invention, the profile of each system component does not have to be stacked on top of the other. By placing (implanting) the two system components in series, the device (valve, anchoring frame, and delivery system) profiles can be significantly reduced without trade-offs in performance to any of the system components. There are other benefits to this approach that will be highlighted later in this specification.

Further features of the invention, its nature and various advantages, will be more apparent from the accompanying drawings and the following detailed description.

BRIEF DESCRIPTION OF THE DRAWINGS

FIG. 5b is a simplified, partial, elevational view of what is shown in FIG. 5a.

FIG. 7b is a simplified top view of the structure shown in FIG. 7a.

FIG. 9a is similar to FIG. 5a.

DETAILED DESCRIPTION

Figure 1A:
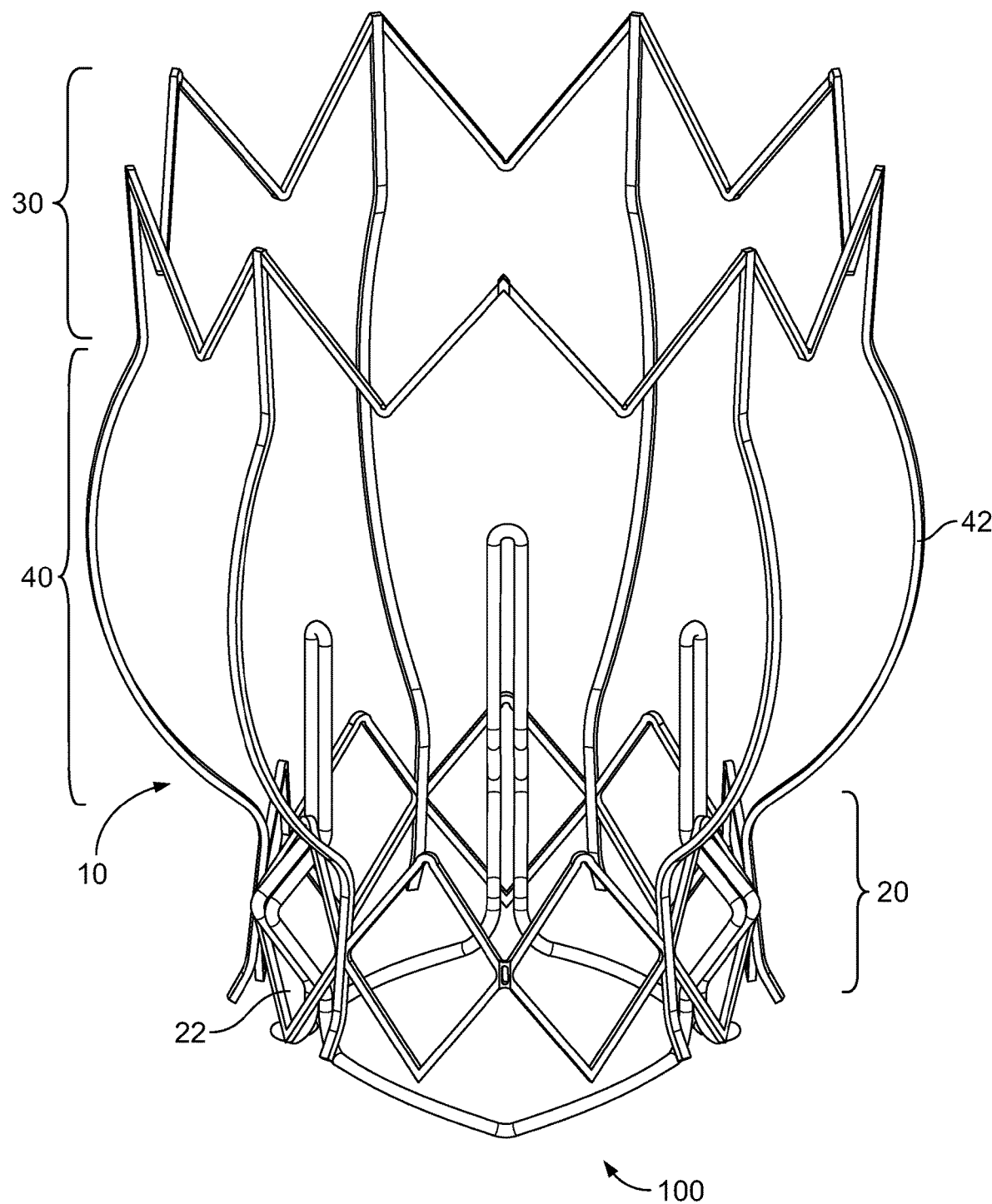
FIG. 1a is a simplified isometric or perspective view of an illustrative embodiment of apparatus in accordance with the invention.

FIG. 1a shows an illustrative embodiment of an anchoring frame 10 and a valve support frame 100, assembled together, but without any of the other components that a valve in accordance with this invention typically includes. Components 10 and 100 are typically made of a highly elastic metal such as nitinol, but can also be made from stainless steel. Each of these components may be laser-cut from a tube and then processed to its final shape and dimensions. Each of components 10 and 100 is preferably a continuous annular (ring) structure. Each of components 10 and 100 is annularly, preferably elastically compressible to a smaller annular or circumferential size for delivery into a patient through instrumentation that can be less invasive than full open-chest, open-heart surgery. For example, delivery of the collapsed structures can be through a tube such as a catheter, a trocar, a laparoscopic instrument, or the like. When each component reaches the implant site in the patient, that component can be released to (preferably) elastically re-expand to the approximate size shown in FIG. 1a. This causes the re-expanded component (and any other components carried by that component) to implant itself in the patient. Anchoring structure 10 is delivered into and implanted in the patient first. Then valve support structure 100 (with valve 200 (FIG. 1b) mounted inside it) is delivered into the patient and implanted inside the already-implanted anchoring structure 10.

Anchoring structure 10 is primarily responsible for holding the valve in place in the patient, in addition to anchoring itself to native anatomy of the patient. Valve support structure 100 includes features that interengage or interlock with features of anchoring structure 10 to hold valve support structure 100 in place relative to anchoring structure 10. In the embodiment shown in FIGS. 1a-b these interlocking features include radial outward projections 112 on the commissure posts 110 of valve support structure 100 fitting into closed-perimeter, open-center cells 22 in the annulus inflow portion 20 of anchoring structure 10.

Figure 1B:
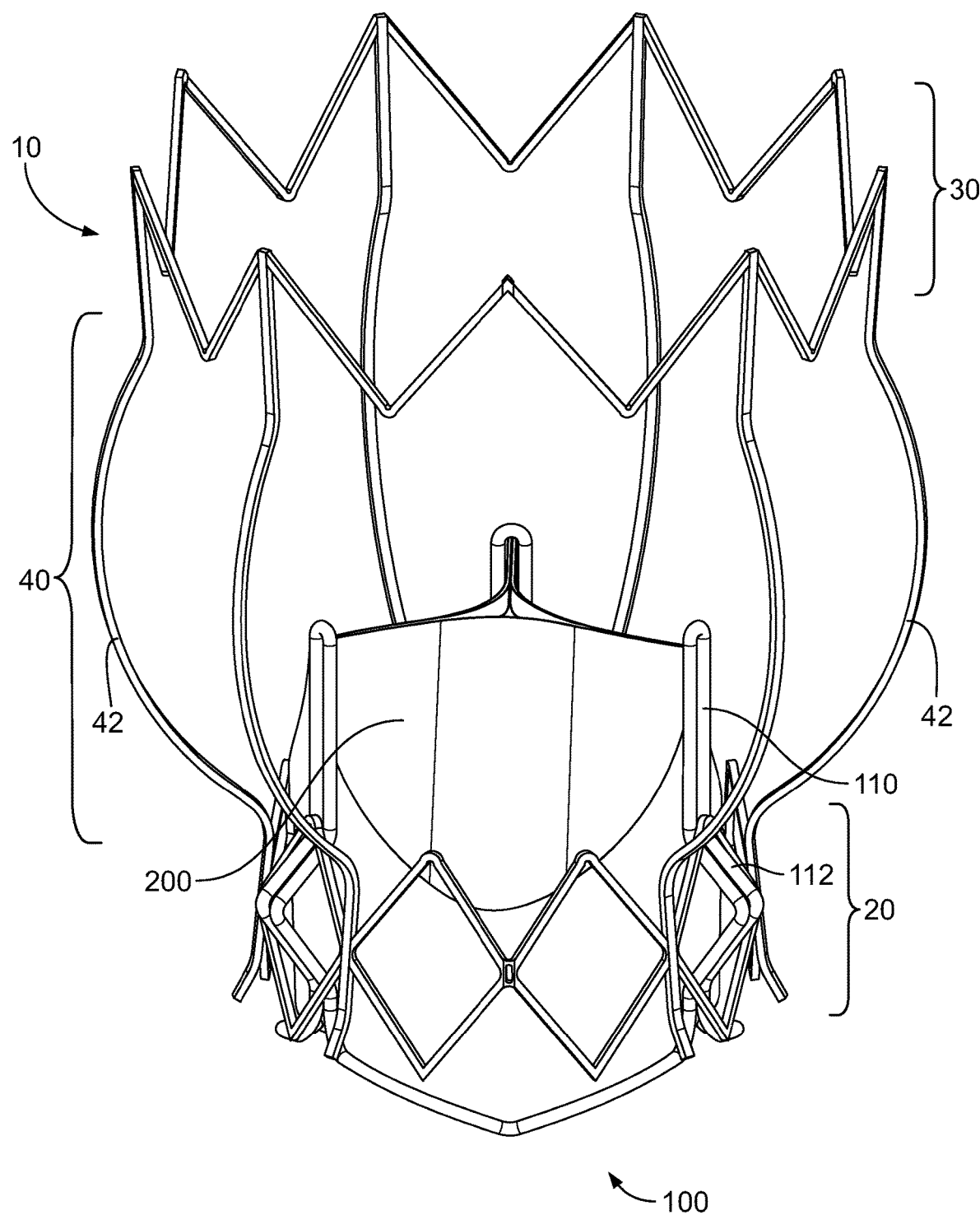
FIG. 1b is similar to FIG. 1a, but shows the addition of more structure to the apparatus.
Figure 2A:
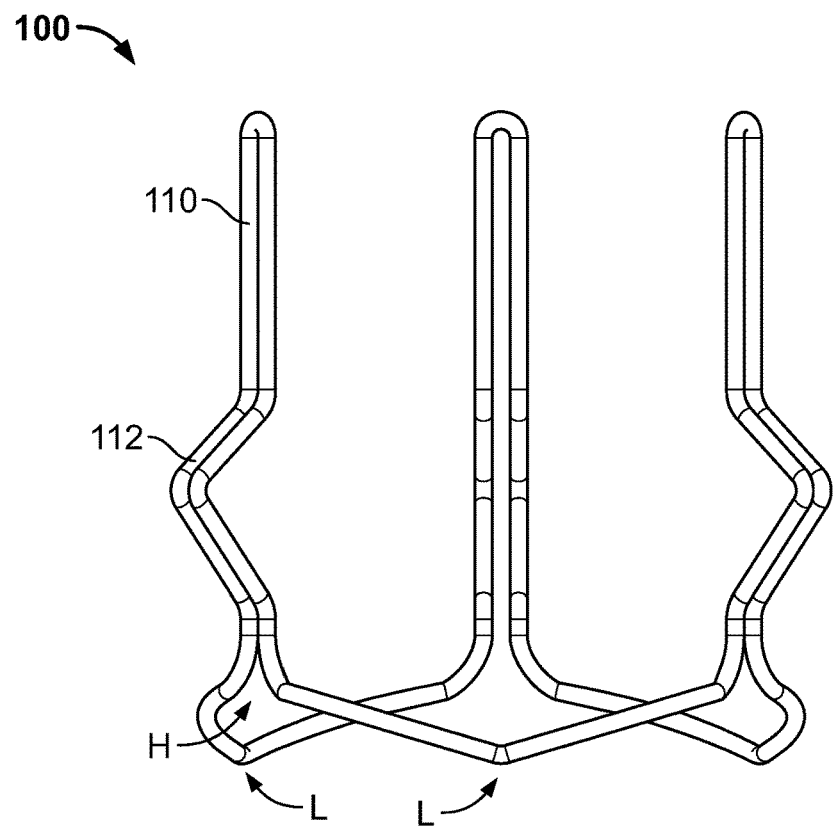
FIG. 2a is a simplified elevational view of an illustrative embodiment of one component from FIGS. 1a and 1b in accordance with the invention.
Figure 2B:
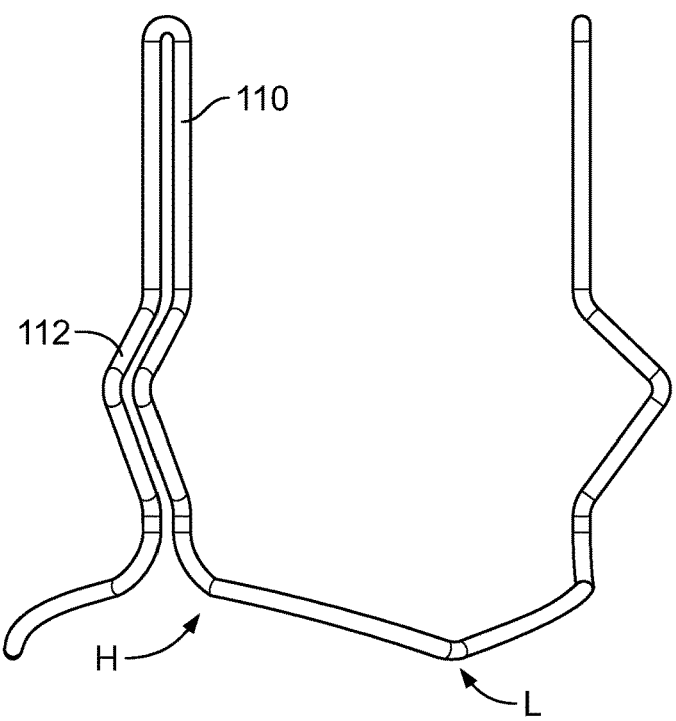
FIG. 2b is a simplified, partial, elevational view of the FIG. 2a component from a different angle.
Figure 2C:
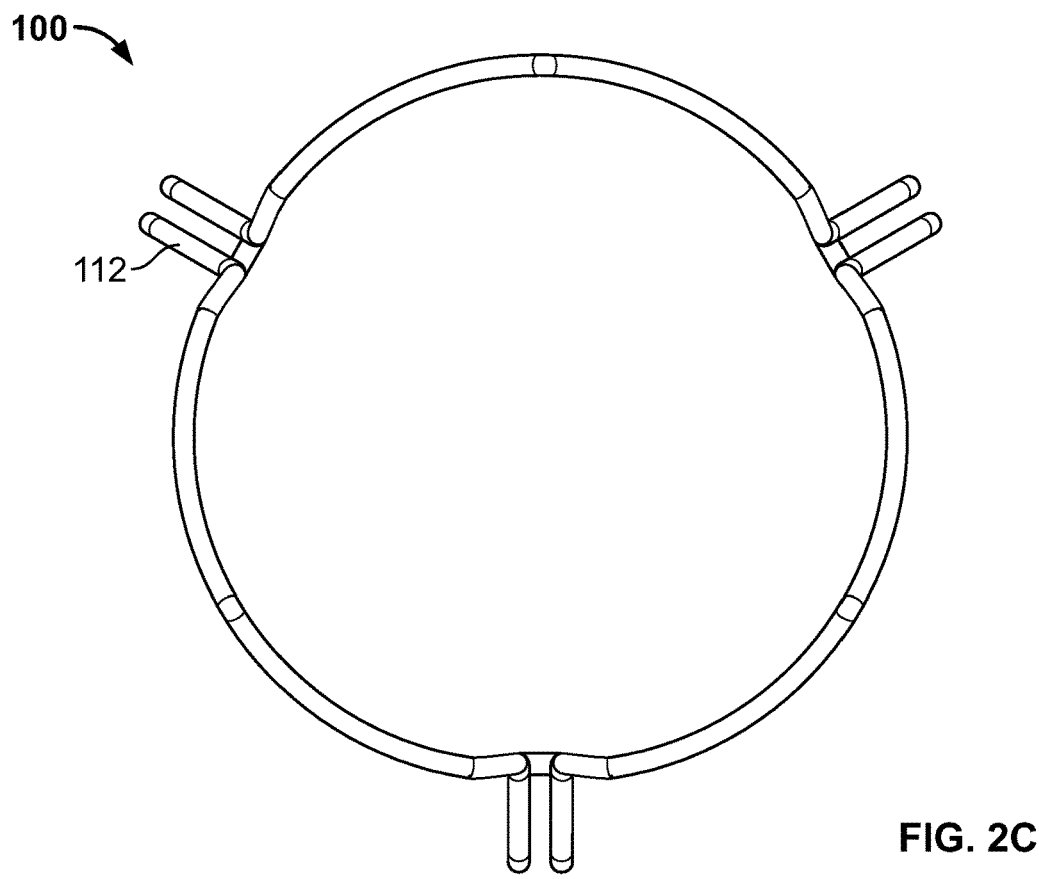
FIG. 2c is a simplified top view of the component of FIGS. 2a and 2b.
Figure 2D:
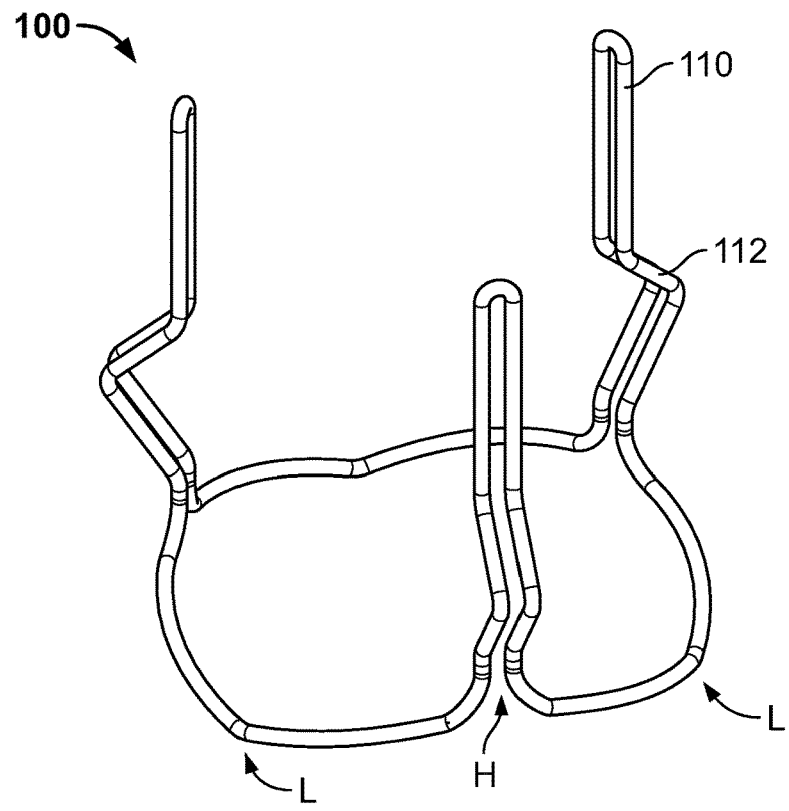
FIG. 2d is a simplified perspective or isometric view of the component of FIGS. 2a-c.

Annulus inflow portion 20 of anchoring structure 10 is typically implanted in or near the patient's native valve annulus. This is the reason for referring to this portion of structure 10 as the annulus inflow portion. ("Inflow" is a term that is used with reference to the direction of blood flow through the prosthetic valve when the valve is in use in a patient. "Outflow" is similarly used with reference to the direction of blood flow through the prosthetic valve.) The embodiment shown in FIGS. 1a-1b is especially adapted for use as a prosthetic aortic valve. Annulus inflow portion 20 is therefore implanted in or near the patient's native aortic valve annulus. An aortic outflow portion 30 of anchoring structure 10 then resides in the patient's aorta. Portions 20 and 30 are connected to one another by connecting strut structure 40, which passes through the patient's valsalva sinus. The connecting struts 42 of structure 40 bulge radially out with an outwardly convex curve into the outwardly bulging lobes of the valsalva sinus to help hold the valve in place in the patient.

Valve or leaflet structure 200 (mounted inside valve support structure 100) typically includes three flexible leaflets that come together to close the valve as shown in FIG. 1b. This occurs when blood pressure above the valve as viewed in FIG. 1b is greater than blood pressure below the valve. When blood pressure below the valve exceeds blood pressure above the valve, the leaflets of the valve are pushed aside to open the valve and allow blood to flow upward through the valve. Suitable materials for leaflets 200 include biological tissue, metal (e.g., thin nitinol), flexible polymers or mesh-reinforced polymers, and the like.

Again, not all components of a finished and implanted valve are shown in FIG. 1b. For example, other layers of material such as tissue, polymer, fabric, buffer material, or the like can be included for such purposes as cushioning other components, promoting tissue ingrowth, etc.

FIGS. 2a-d show an illustrative embodiment of a valve support structure 100 by itself from several directions. (FIG. 1b shows only part of that structure.) A possible feature brought out by these FIGS. is the scalloped inflow edge of structure 100. (Again, inflow refers to the direction of blood flow through the valve when in use in a patient.) The anchoring frame 10 may also be similarly scalloped. By "scalloped" it is meant that the inflow edge is relatively high near the base of at least one (preferably all) of the commissures of the patient's native heart valve, and also the commissures 110 of the prosthetic valve. A typical high area is pointed to from the reference letter H. Elsewhere the inflow edge can be relatively low (pointed to from the reference letter L). "High" means that such a portion of the inflow edge is closer to the geometric plane defined by the distal free ends or tips of commissure posts 110. "Low" means that such a portion of the inflow edge is farther from that geometric plane. Making one or more portions of the inflow edge high as described above helps the implanted valve avoid impinging on the patient's native mitral valve and other structures in the heart that are adjacent the aortic valve (e.g., conduction system pathways and the AV node).

Figure 3A:
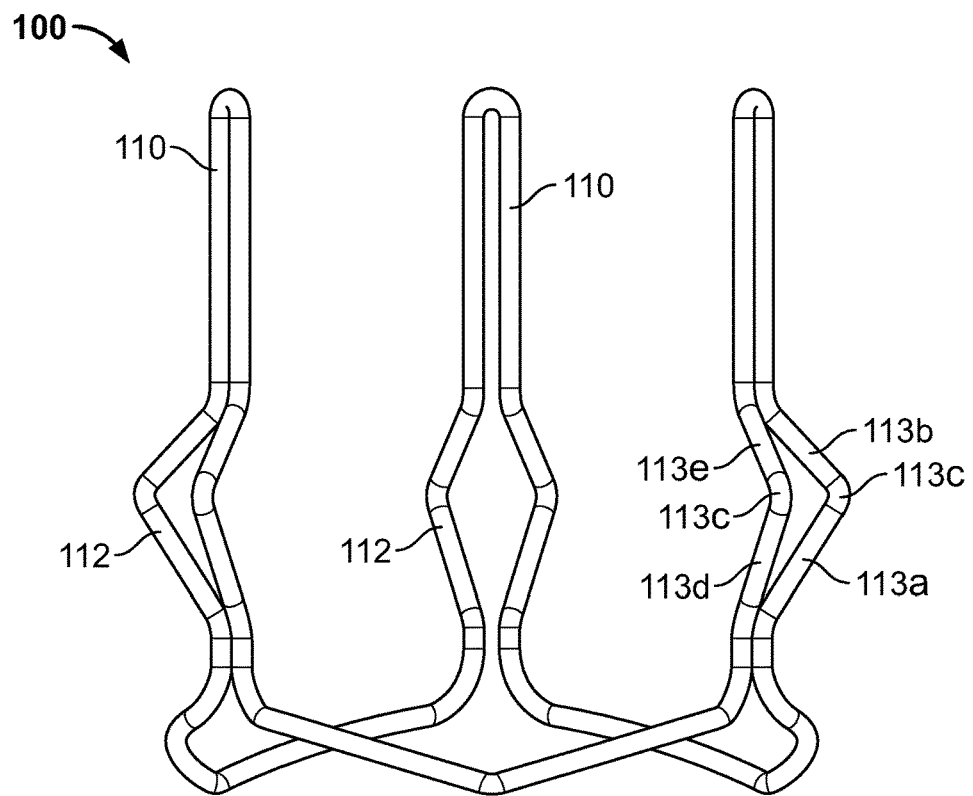
FIG. 3a is a view similar to FIG. 2a, but for another illustrative embodiment in accordance with the invention.
Figure 3B:
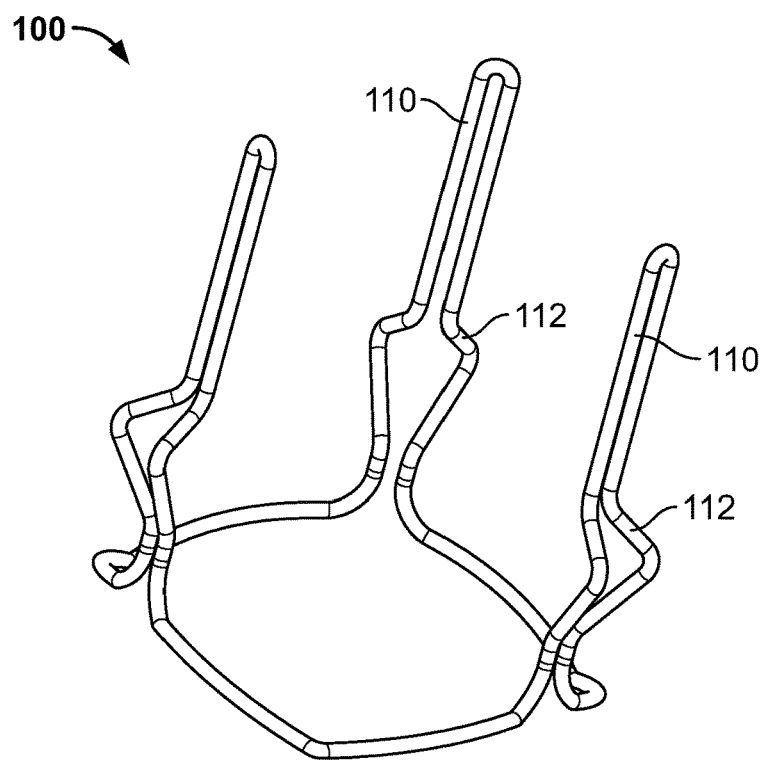
FIG. 3b is a simplified perspective or isometric view of the FIG. 3a structure.

FIGS. 3a-b show another illustrative embodiment of a valve support structure 100 by itself from different directions. A possible feature brought out by these FIGS. is the provision of what may be called spread elbows for outward projections 112. This means that the two members that make up each commissure post 110 diverge from one another in the annular direction where they extend radially out to form a projection 112. This can help to improve stability of engagement between structures 10 and 100 in an implanted valve.

FIGS. 3a-b (and also other FIGS.) illustrate the concept that valves of this invention can employ what may be termed independent flexing commissure posts 110. At least above outward projections 112, commissure posts 110 can be free of contact with anchoring structure 10 when components 10 and 100 are interlocked together. Commissure posts 110 are therefore cantilevered to their free end tips and can accordingly flex independently of one another and other stent-like structure (e.g., 10) of the valve. This can help relieve stress on valve structure 200 and has many other potential benefits.

Figure 4A:
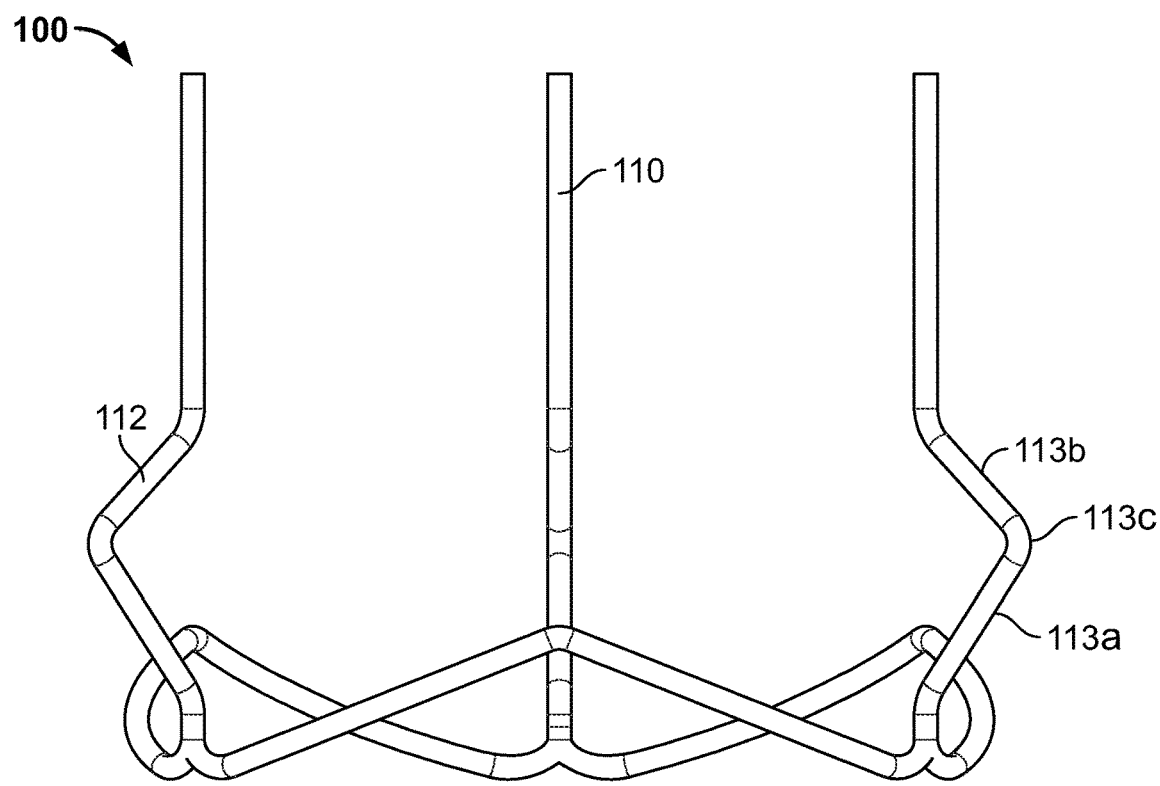
FIG. 4a is a view similar to FIG. 3a, but for another illustrative embodiment in accordance with the invention.
Figure 4B:
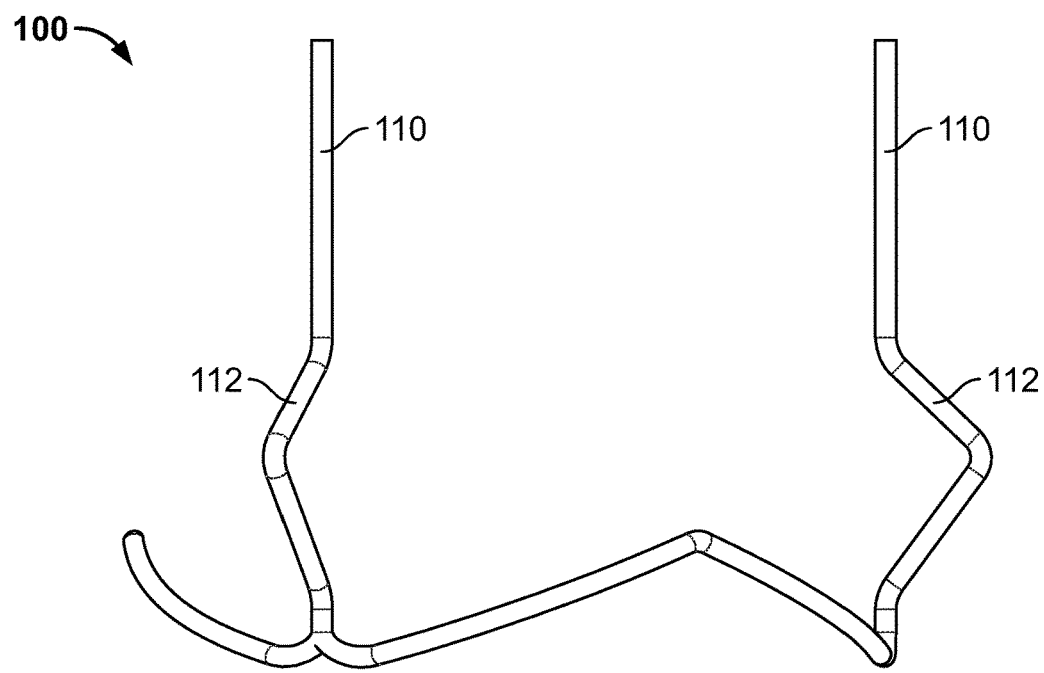
FIG. 4b is a simplified, partial, elevational view of the FIG. 4a structure from a different angle.
Figure 4C:
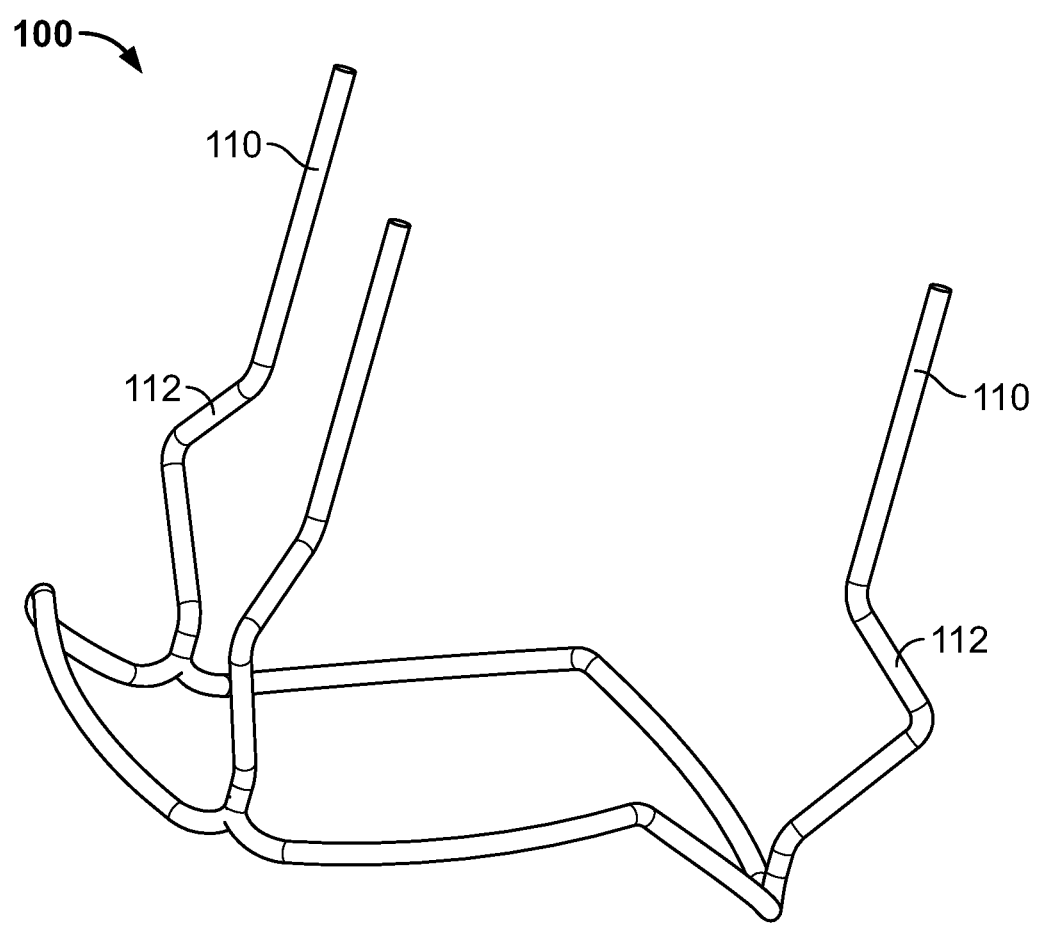
FIG. 4c is a simplified perspective or isometric view of the structure shown in FIGS. 4a and 4b.

FIGS. 4a-c show another illustrative embodiment of a valve support structure 100 in accordance with the invention. In this embodiment each commissure post 110 is effectively a single member. Also, the inflow edge is inverted in the up-down direction as compared, for example, to the inflow edge of the structures 100 shown in earlier FIGS.

Figure 5A:
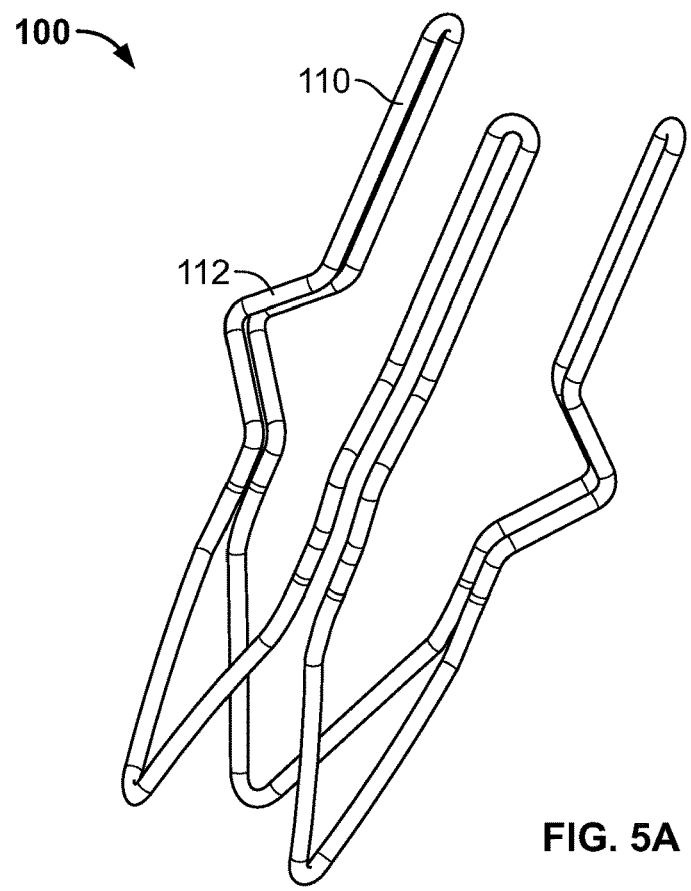
FIG. 5a is a simplified perspective or isometric view of a structure like that shown in FIG. 2a in another operating condition in accordance with the invention.
Figure 5B:
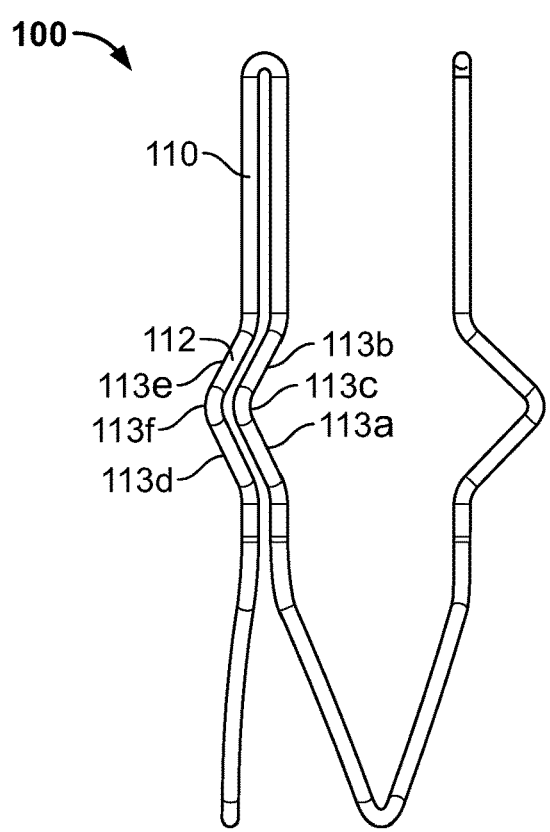
Figure 5C:
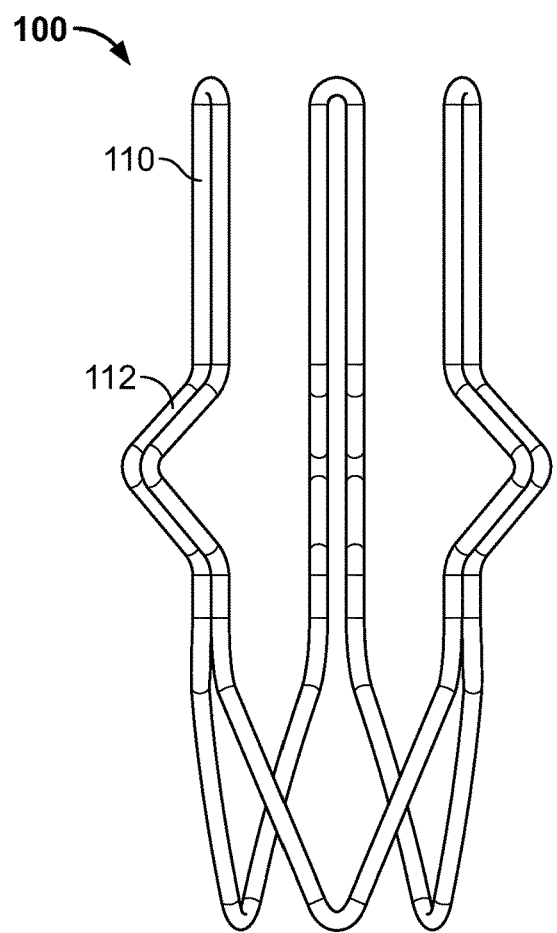
FIG. 5c is a simplified elevational view of the FIGS. 5a-b structure from another angle.
Figure 5D:
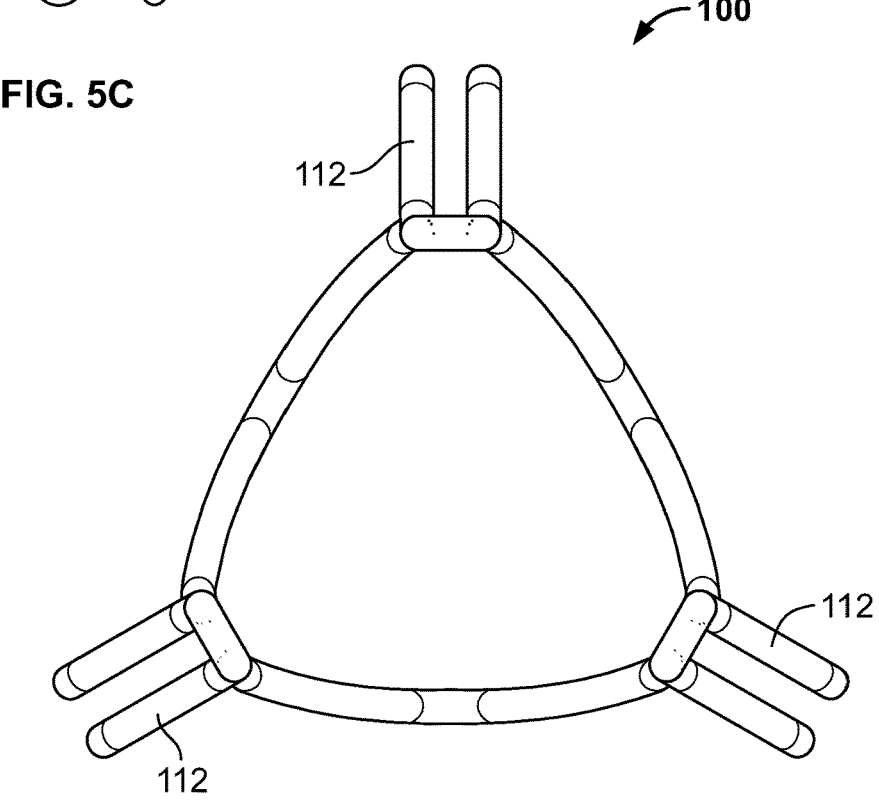
FIG. 5d is a simplified top view of the FIGS. 5a-c structure.

FIGS. 5a-d show several views of an annularly or circumferentially compressed or collapsed valve support structure 100 in accordance with the invention. FIG. 5b is only partial, and FIG. 5d is a top view.

Figure 6A:
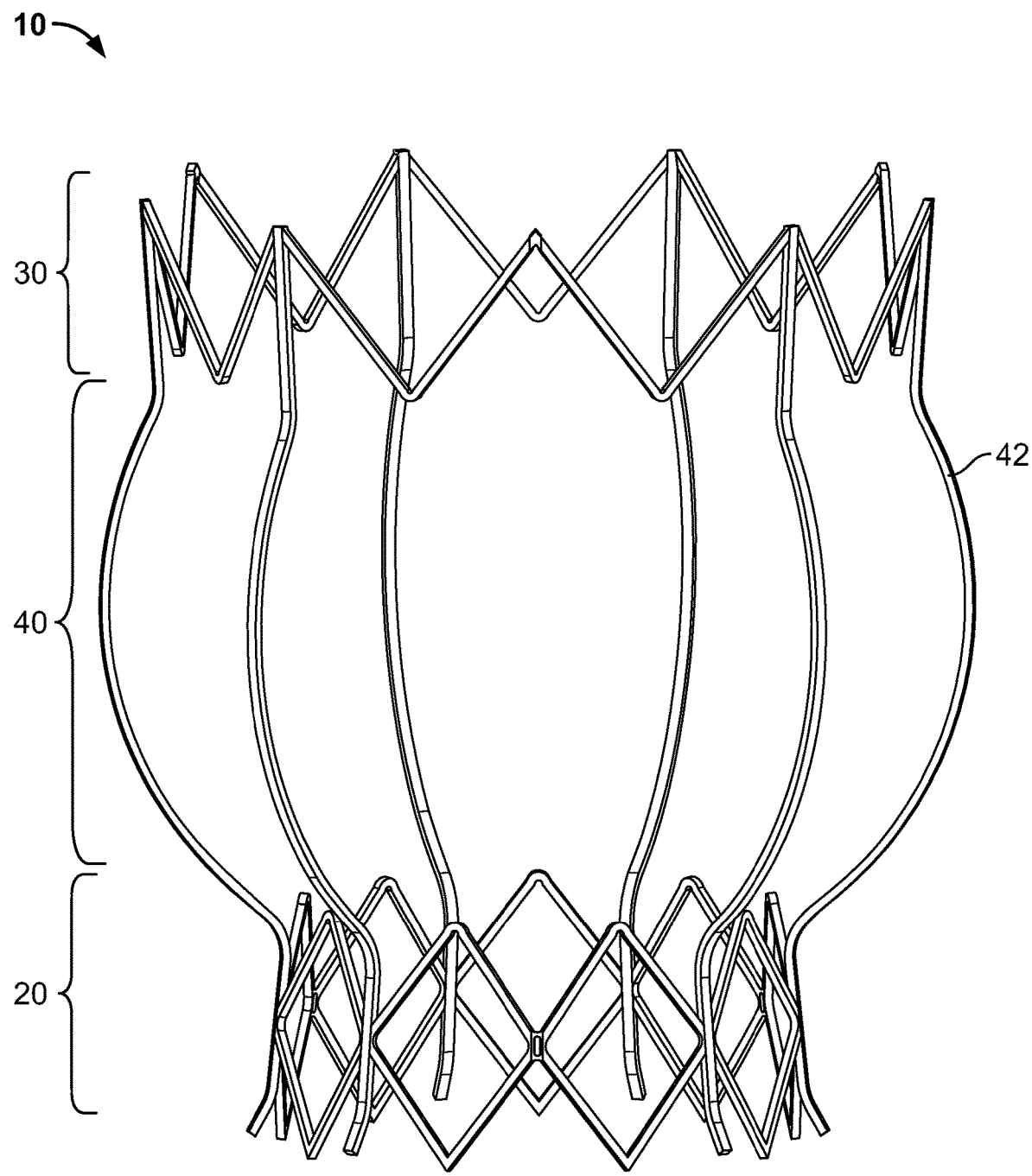
FIG. 6a is a simplified isometric or perspective view of an illustrative embodiment of another component from FIGS. 1a and 1b in accordance with the invention.
Figure 6B:
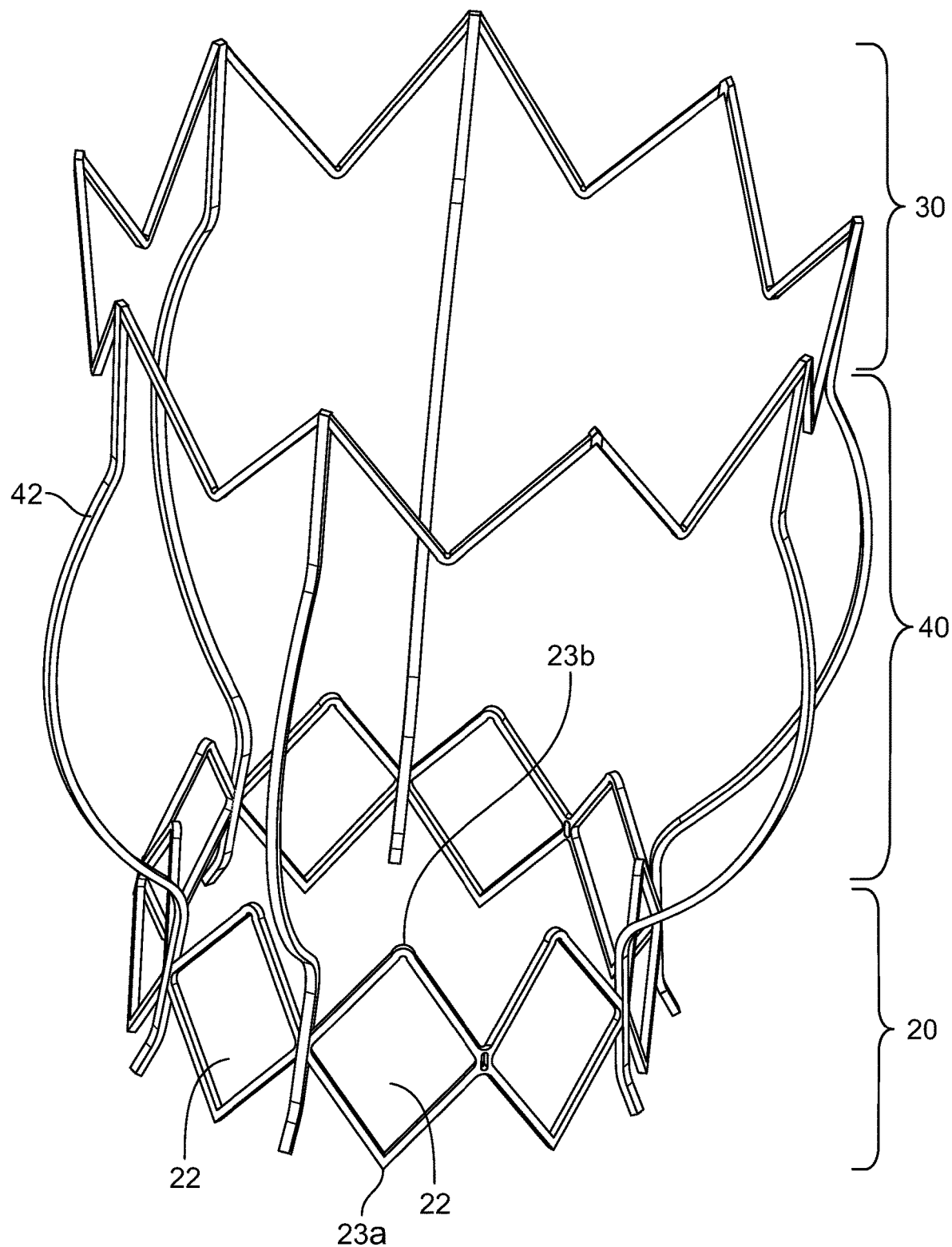
FIG. 6b is another simplified isometric or perspective view of the FIG. 6a structure from another angle.

FIGS. 6a-b show two views of an illustrative embodiment of anchoring structure 10 by itself.

Figure 7A:
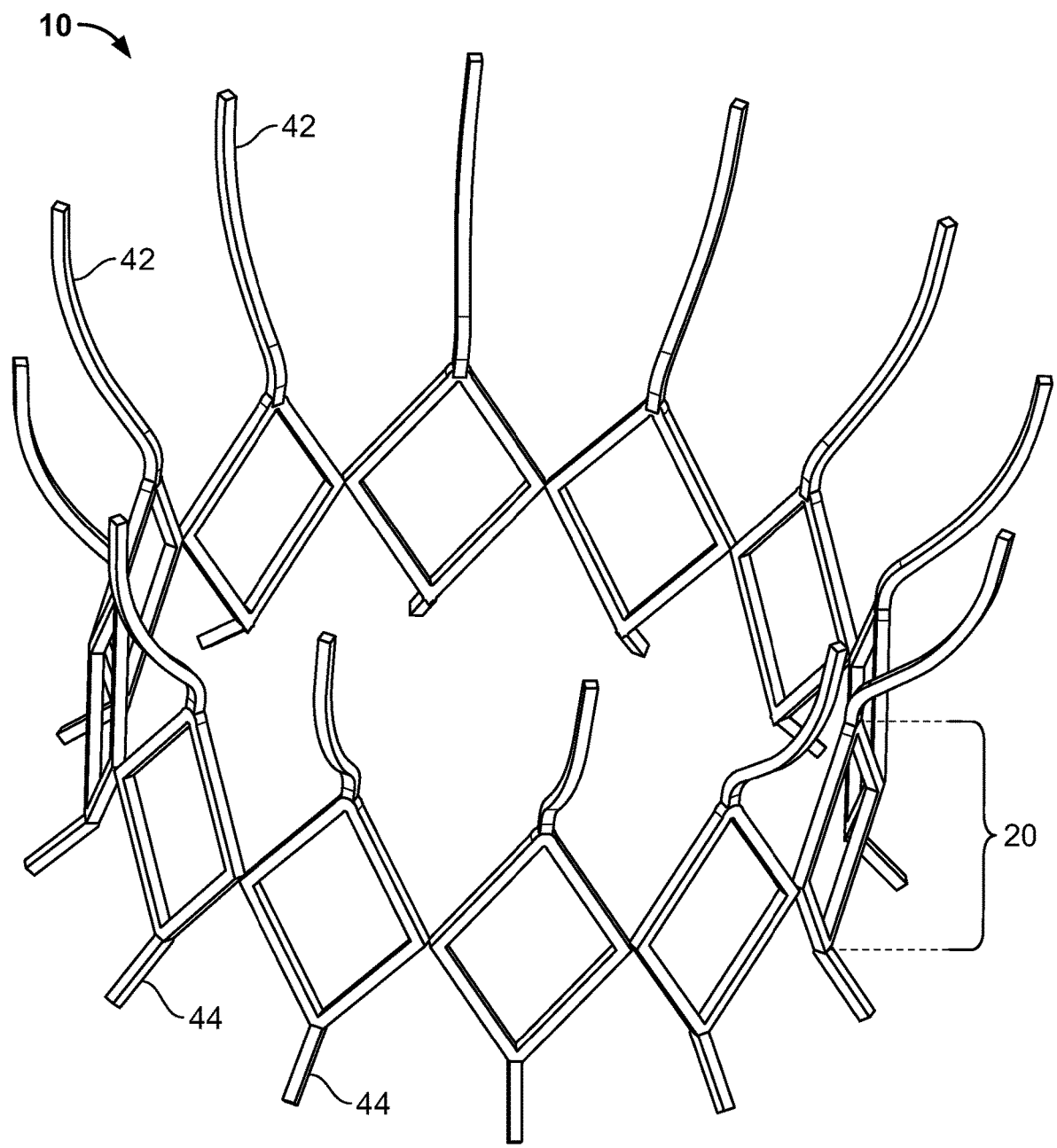
FIG. 7a is a view similar to FIG. 6b for another illustrative embodiment in accordance with the invention.
Figure 7B:
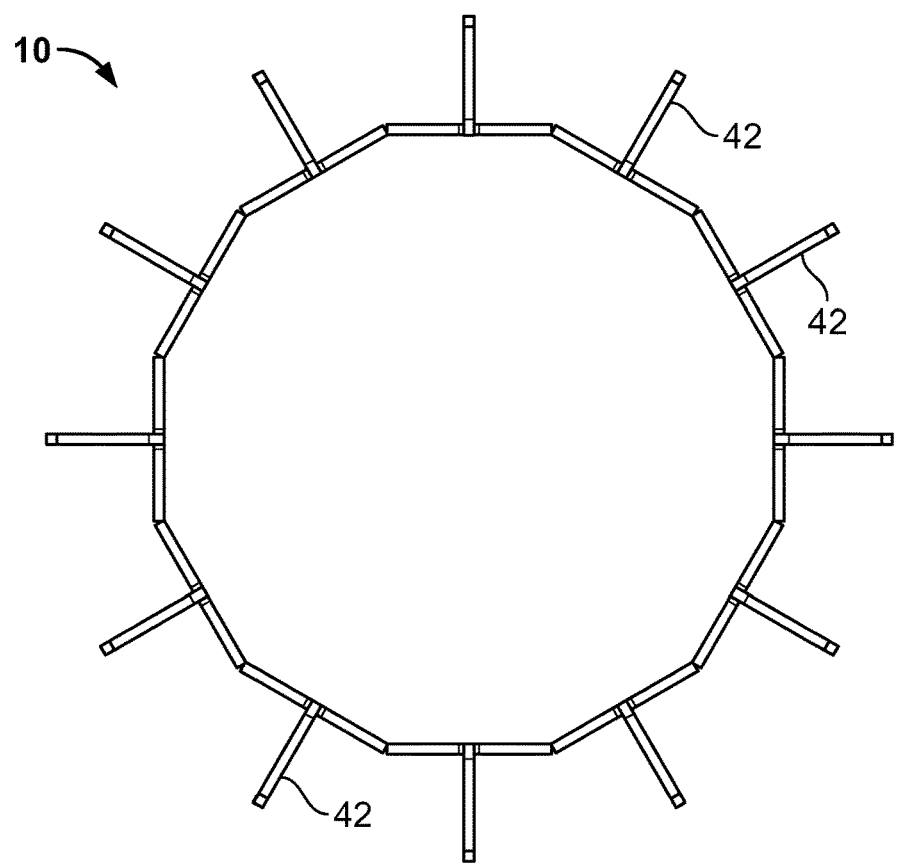
Figure 7C:
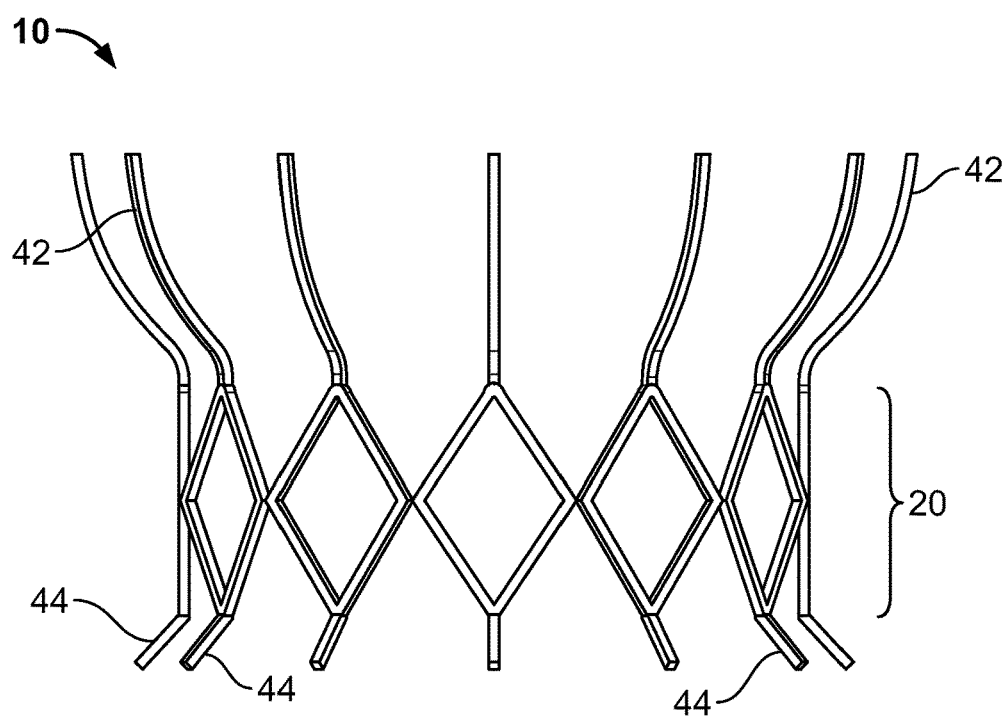
FIG. 7c is a simplified, partial, elevational view of the structure shown in FIGS. 7a-b.

FIGS. 7a-c show several views of an illustrative embodiment of what may be referred to as a short anchoring structure 10. This latter type of anchoring structure includes only annulus inflow portion 20 and truncated struts 42 extending up from annulus inflow portion 20 into a portion of the patient's valsalva sinus.

Figure 8A:
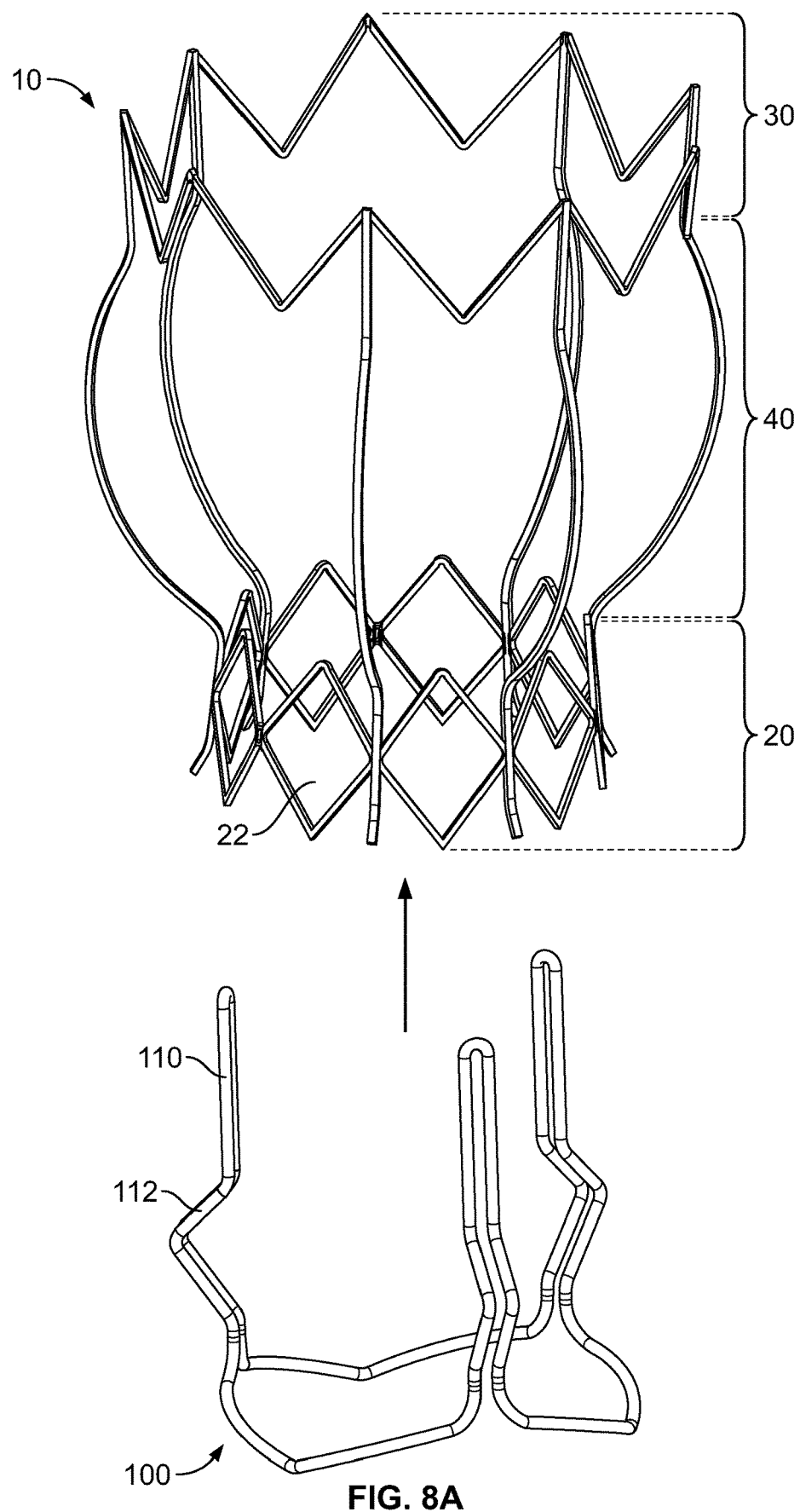
FIG. 8a is a view generally similar to FIG. 1a, but shows an illustrative embodiment of how the FIG. 1a components may be assembled in accordance with the invention.
Figure 8B:
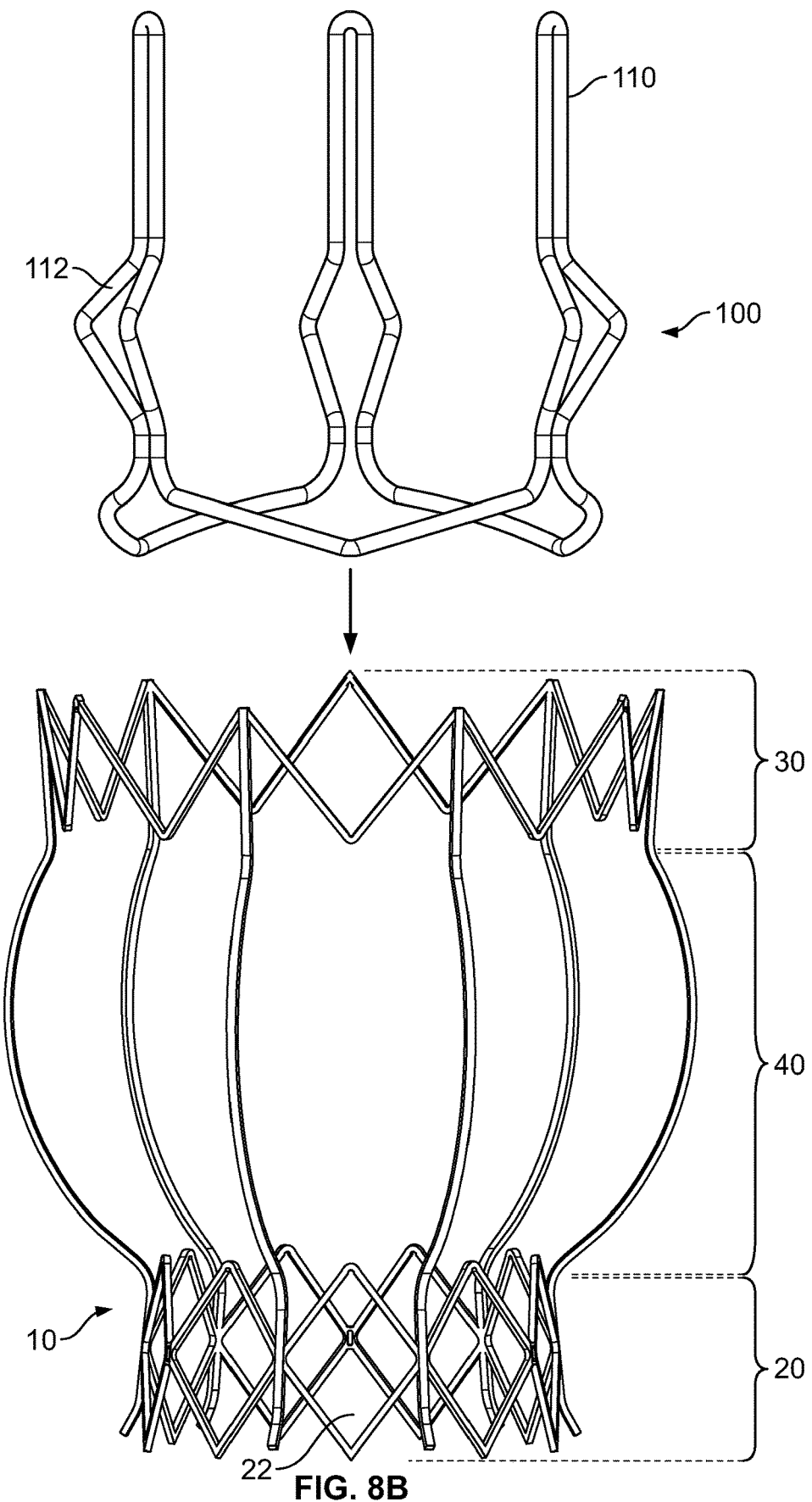
FIG. 8b is a simplified elevational view of the FIG. 8a structure, but shows another illustrative embodiment of how the FIG. 1a components may be assembled in accordance with the invention.

FIGS. 8a-b show two ways of implanting component 100 into component 10 in a patient. (Component 10 is assumed to be already implanted at the desired location in the patient.) In FIG. 8a valve frame structure 100 is delivered into anchoring structure 10 from the inflow end of structure 10. In FIG. 8b valve frame 100 is delivered into anchoring structure 10 from the outflow end of structure 10.

Figure 9A:
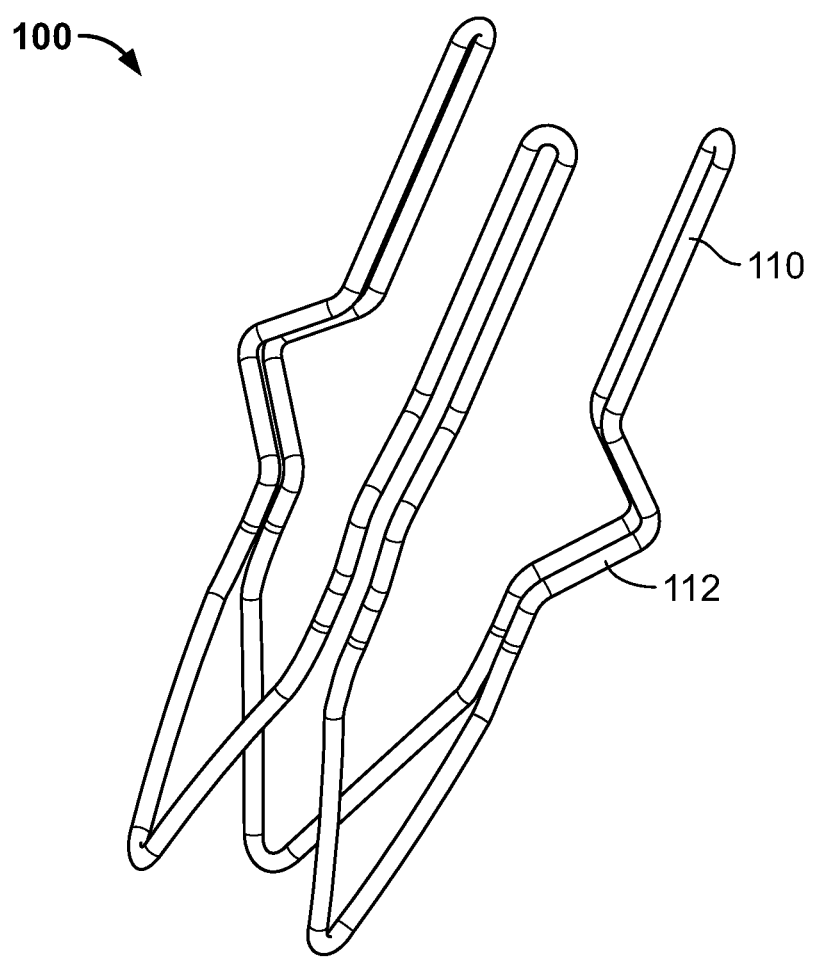
Figure 9B:
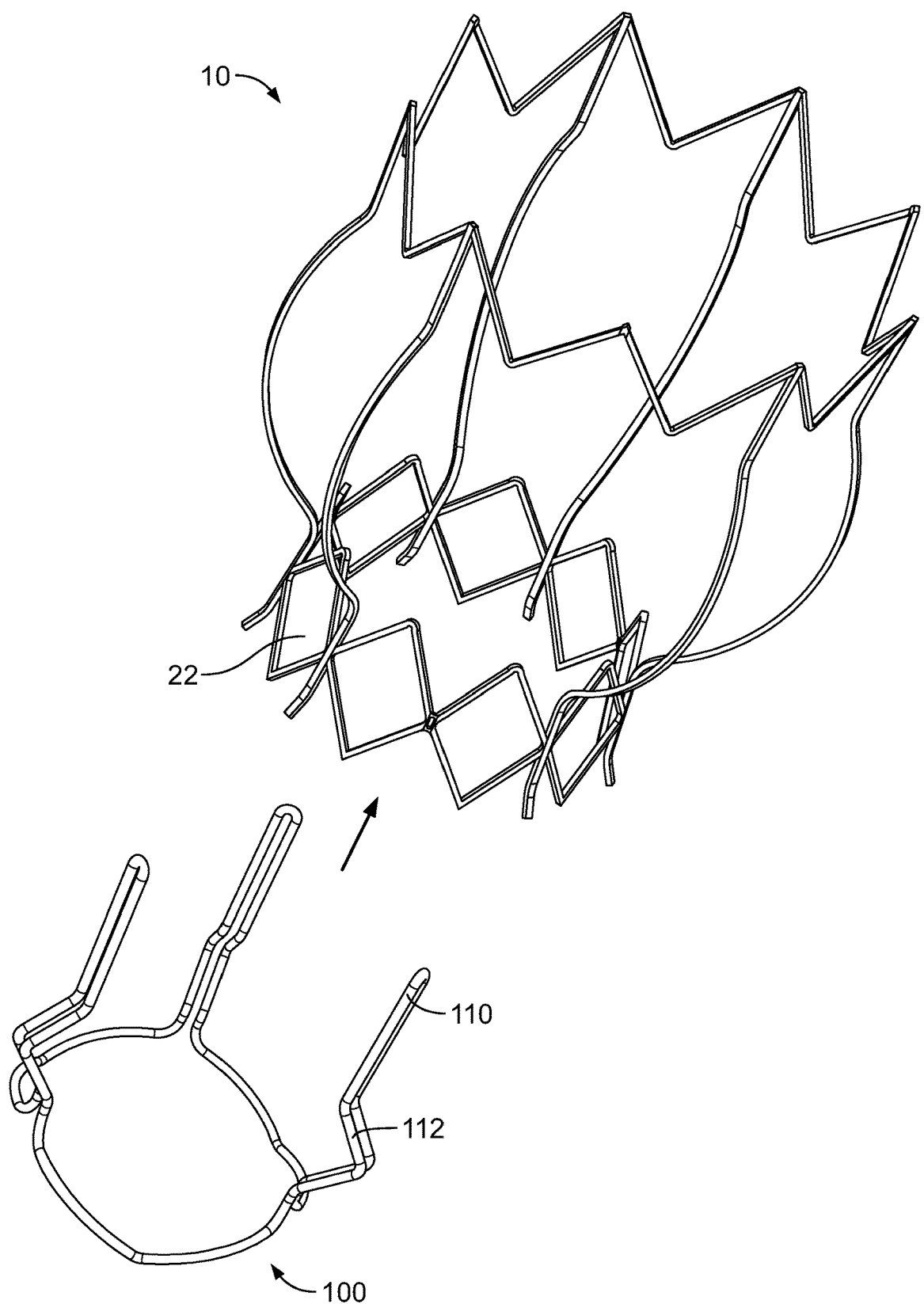
FIG. 9b is similar to FIG. 8a, but shows the structure from another angle.
Figure 9C:
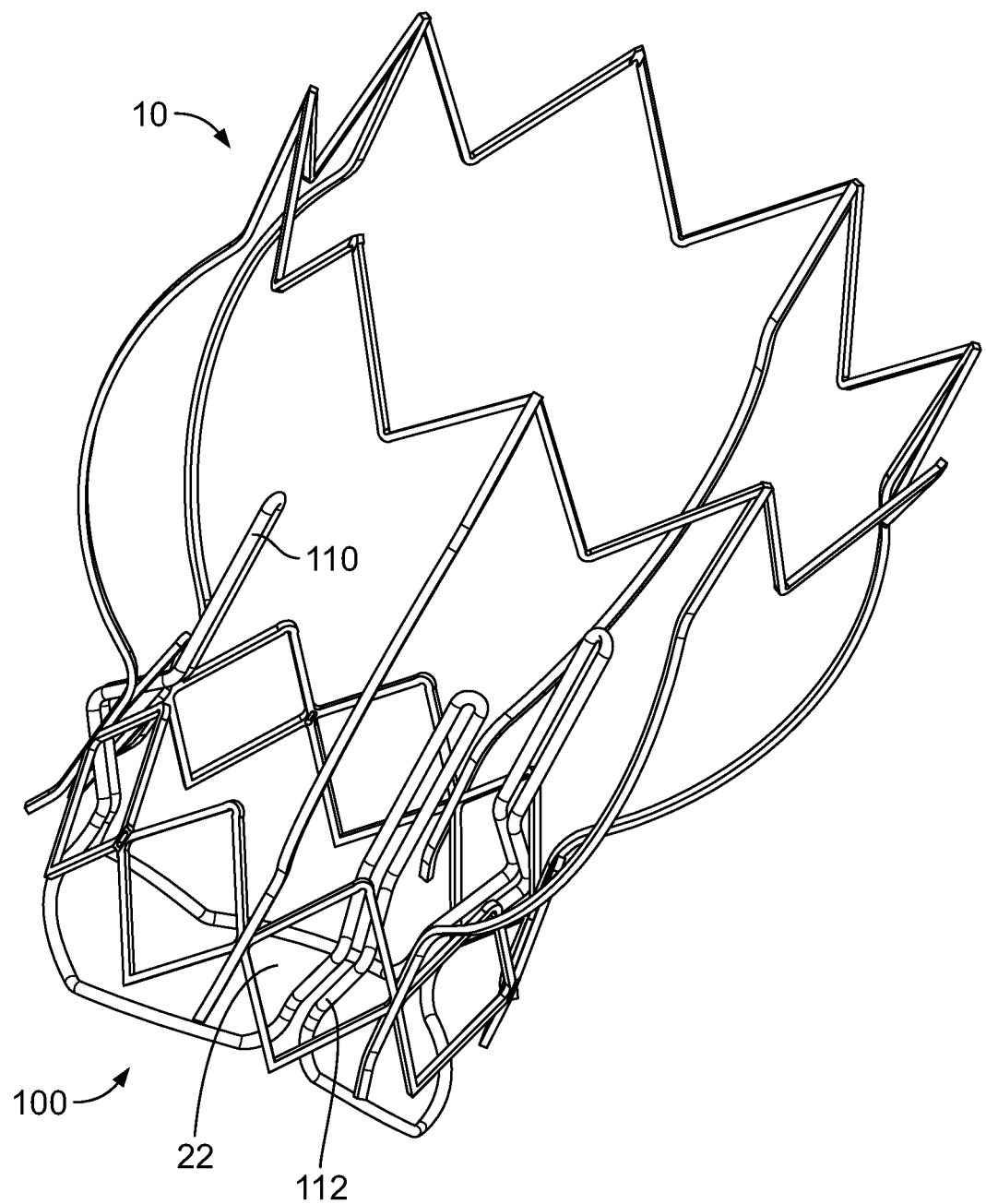
FIG. 9c is similar to FIG. 1a, but shows the structure from another angle.

FIGS. 9a-c show an illustrative embodiment of delivery of valve support structure 100 into anchoring structure 10 in accordance with the invention. In FIG. 9a valve support structure 100 is annularly compressed for delivery into the patient. In FIG. 9b structure 100 is released to re-expand as it approaches the inflow end of already-implanted structure 10. In FIG. 9c structure 100 is pushed into structure 10 via the inflow end of structure 10. Structure 100 latches into structure 10 by means of projections 112 on structure 100 projecting radially out into cells 22 in structure 10.

Figure 10A:
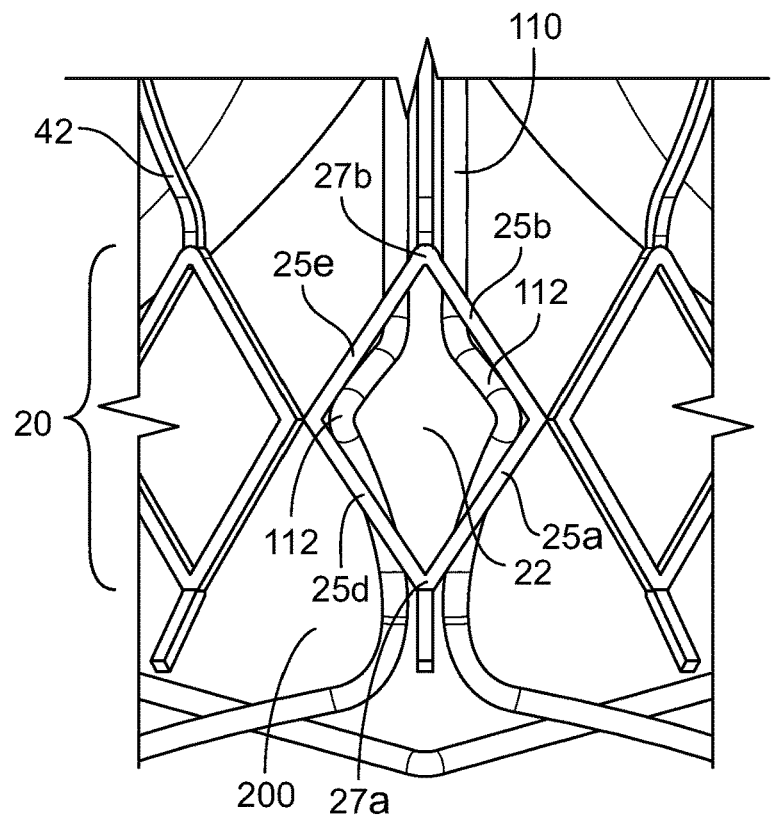
FIG. 10a is a simplified, partial, elevational view of an illustrative embodiment of use of structure like that shown in FIGS. 3a-b in accordance with the invention.
Figure 10B:
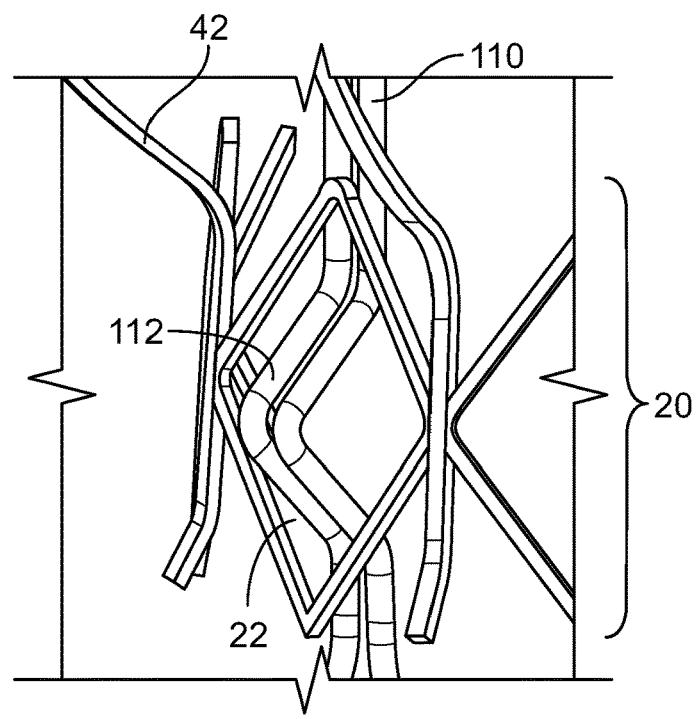
FIG. 10b is a view somewhat like FIG. 10a for another illustrative embodiment of the invention.
Figure 11A:
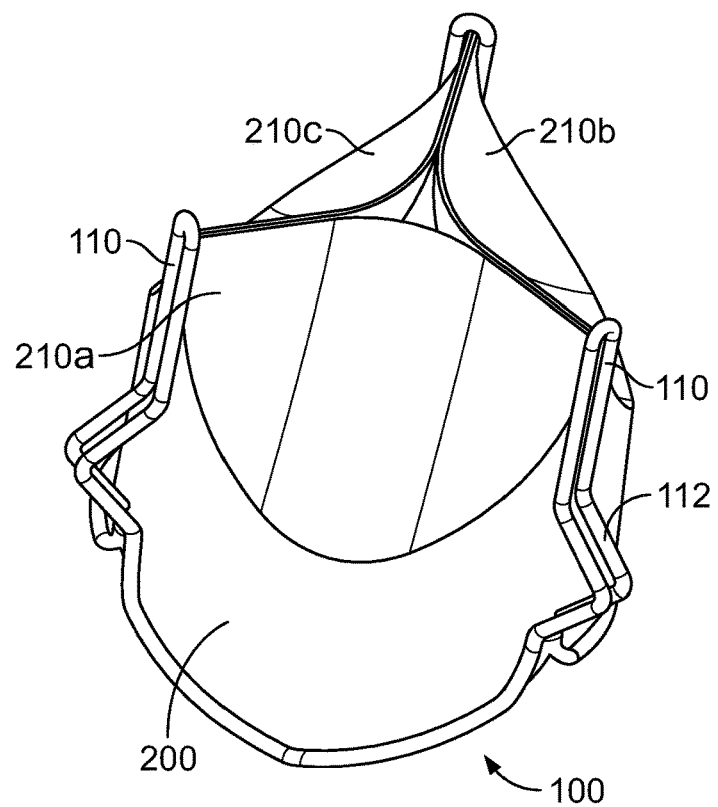
FIG. 11a is a simplified perspective or isometric view of an illustrative embodiment of components that can be used in accordance with the invention.
Figure 11B:
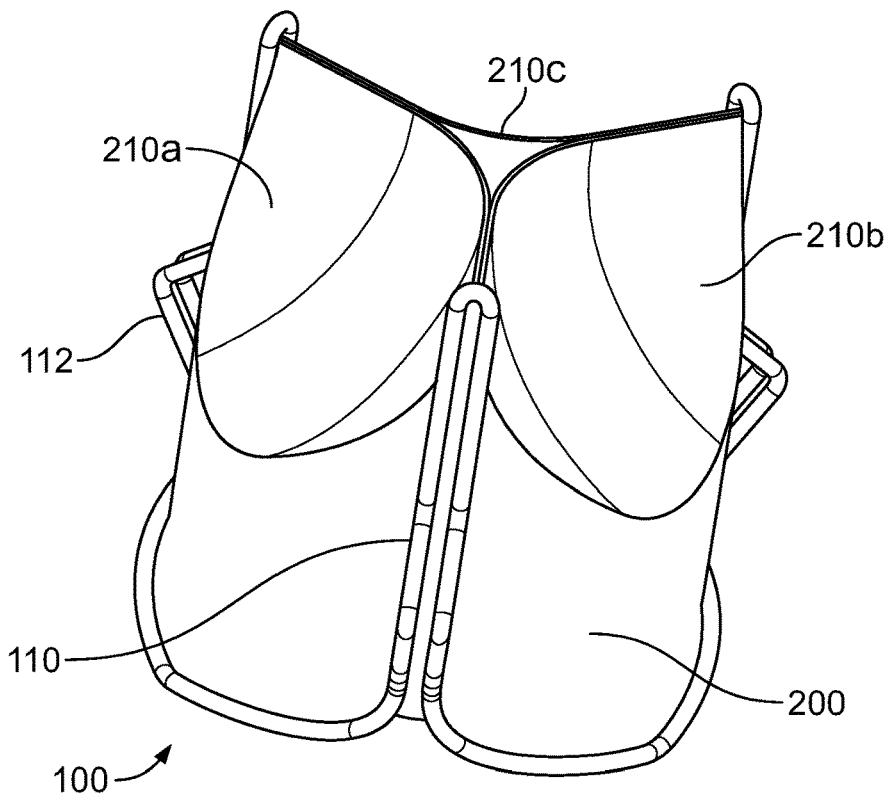
FIG. 11b is similar to FIG. 11a, but shows the structure from another angle.
Figure 11C:
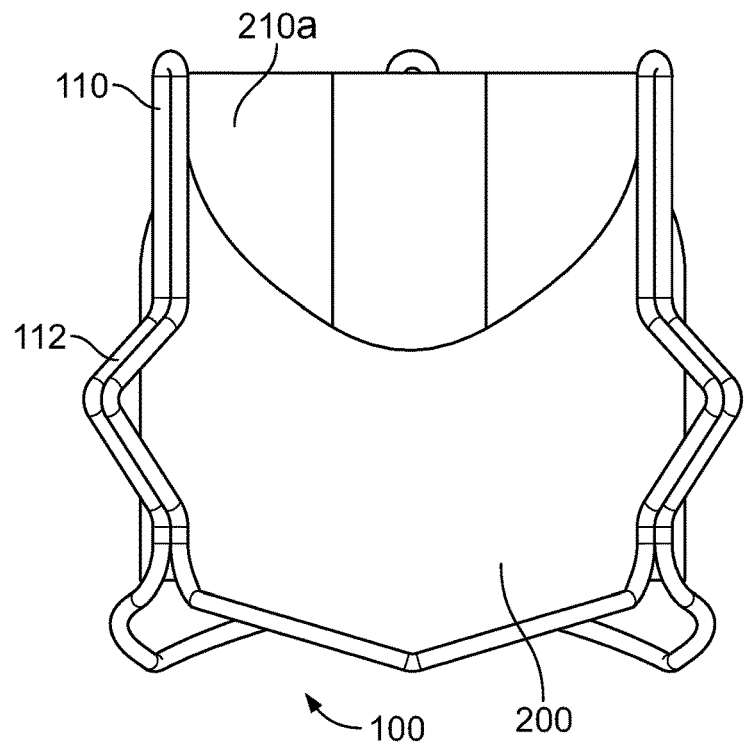
FIG. 11c is a simplified elevational view of the FIGS. 11a-b structure.
Figure 11D:
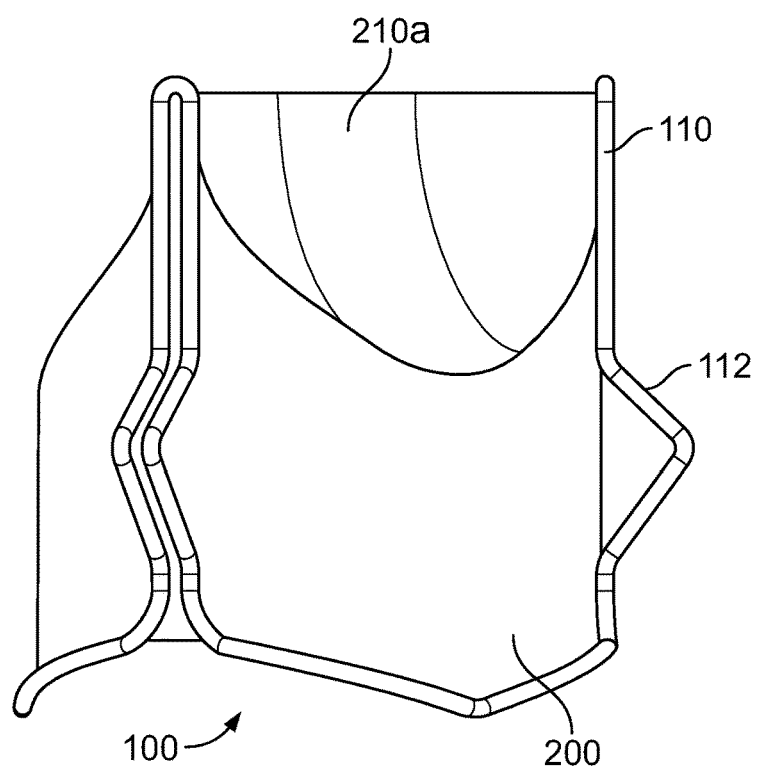
FIG. 11d is similar to FIG. 11c, but shows the structure from another angle.

FIGS. 10a-b show details of the interlocking engagement between outward projections 112 on structure 100 and cells 22 in structure 10. FIG. 10a shows this detail for a spread-elbow embodiment like that shown in FIGS. 3a-b. FIG. 10b shows this detail for another embodiment like that shown in FIGS. 9a-c.

Figure 14:
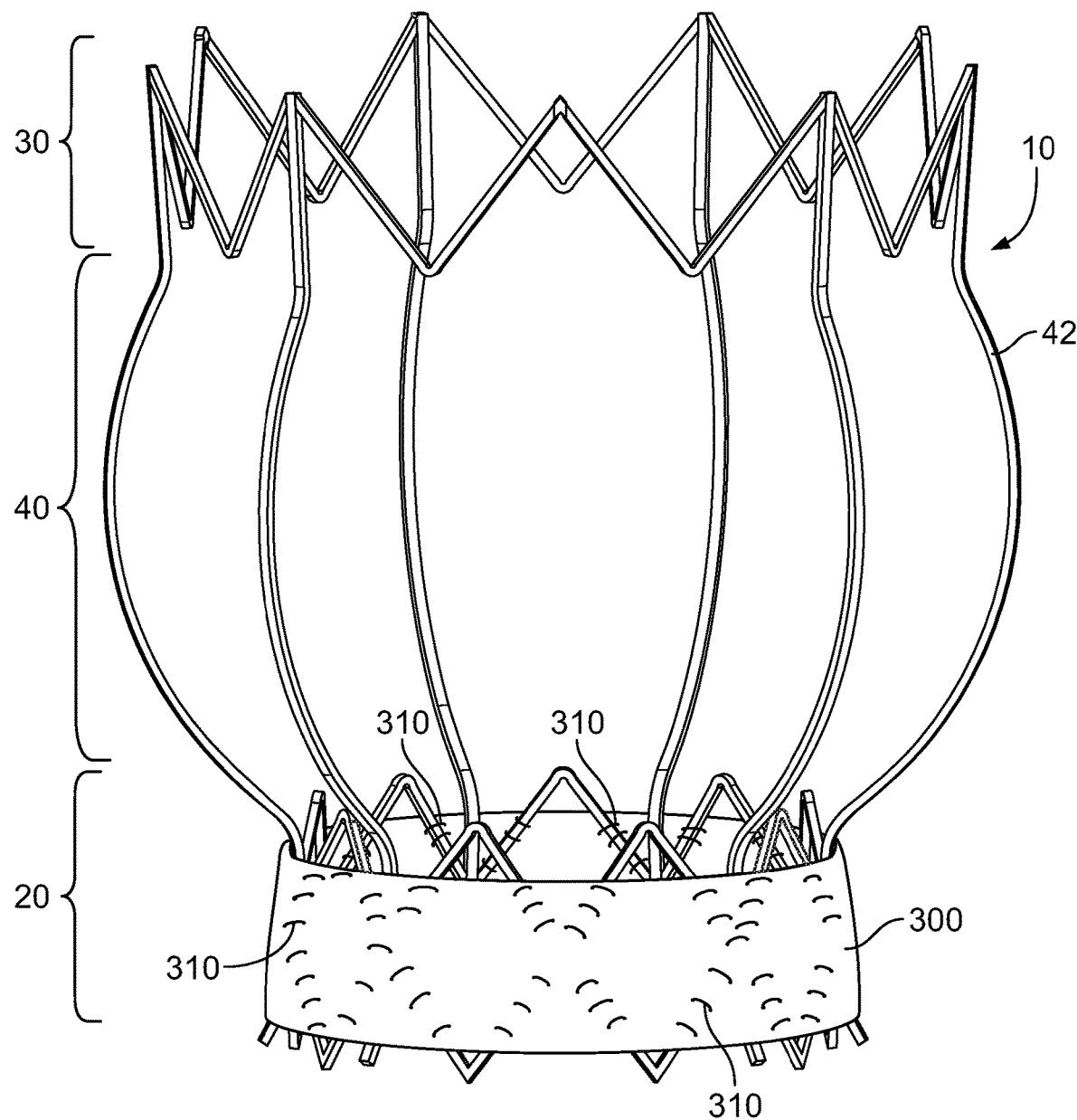
FIG. 14 is similar to FIG. 6a for an illustrative embodiment with other possible components added.
Figure 15:
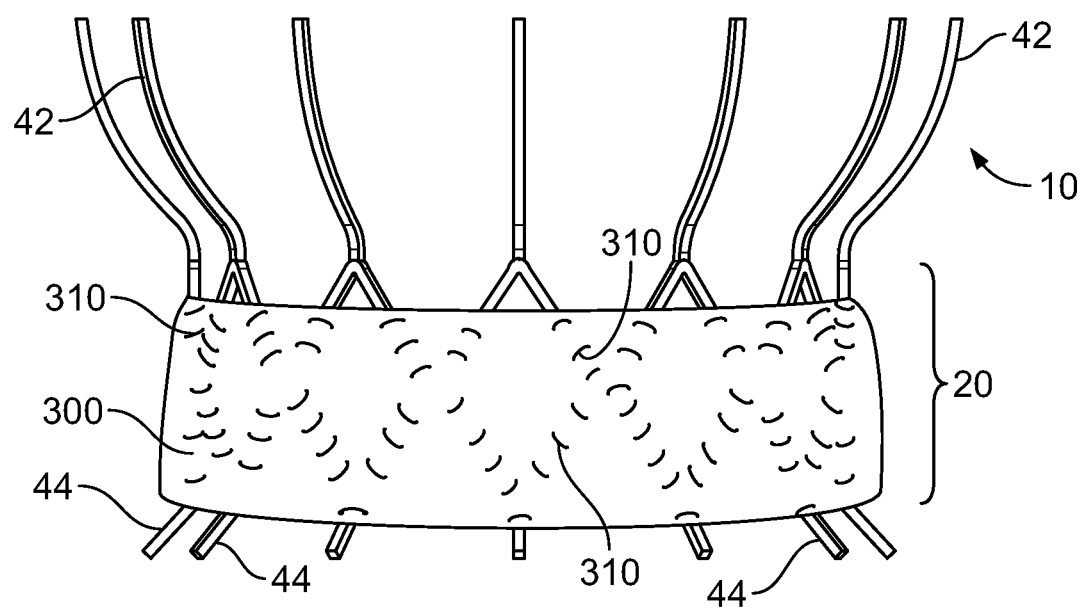
FIG. 15 is similar to FIG. 7c for an illustrative embodiment with other possible components added.

FIGS. 11a-d provide more information about how valve structure 200 may be mounted in valve support structure or frame 100. The three leaflets of valve structure 200 are identified by reference numbers 210a, b, and c. If desired, a cuff (e.g., of fabric and/or tissue sheet material) can be integrated onto the valve assembly to promote tissue ingrowth and to help seal the valve to prevent perivalvular leakage. See, for example, FIG. 14, which shows an illustrative embodiment of such a cuff 300 secured around the outside of the annulus portion 20 of an anchoring frame 10 like that shown in FIG. 6a. As another example, FIG. 15 shows an illustrative embodiment of a cuff 300 secured around the outside of the annulus portion 20 of a short anchoring structure 10 like that shown in FIG. 7c. In each of FIGS. 14 and 15 the cuff 300 may be secured to the underlying structure (e.g., 10) with suture material 310 that passes through the cuff material and loops around adjacent portions of the frame structure 10. Although FIGS. 14 and 15 show cuff 300 extending annularly around the outside of frame structure 10, an alternative is for cuff 300 to extend annularly around the inside of the frame structure.

Figure 12A:
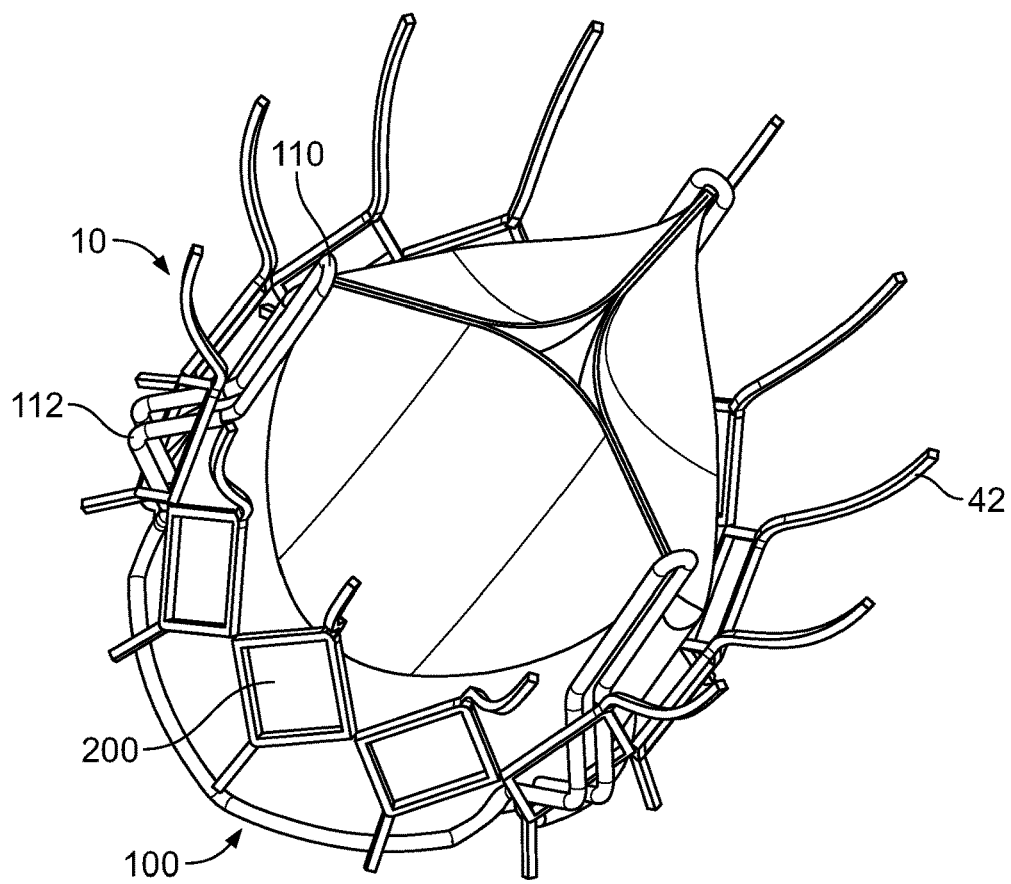
FIG. 12a is somewhat like FIG. 11a, but shows an illustrative use of the FIG. 12a structure with an illustrative embodiment of another component in accordance with the invention.
Figure 12B:
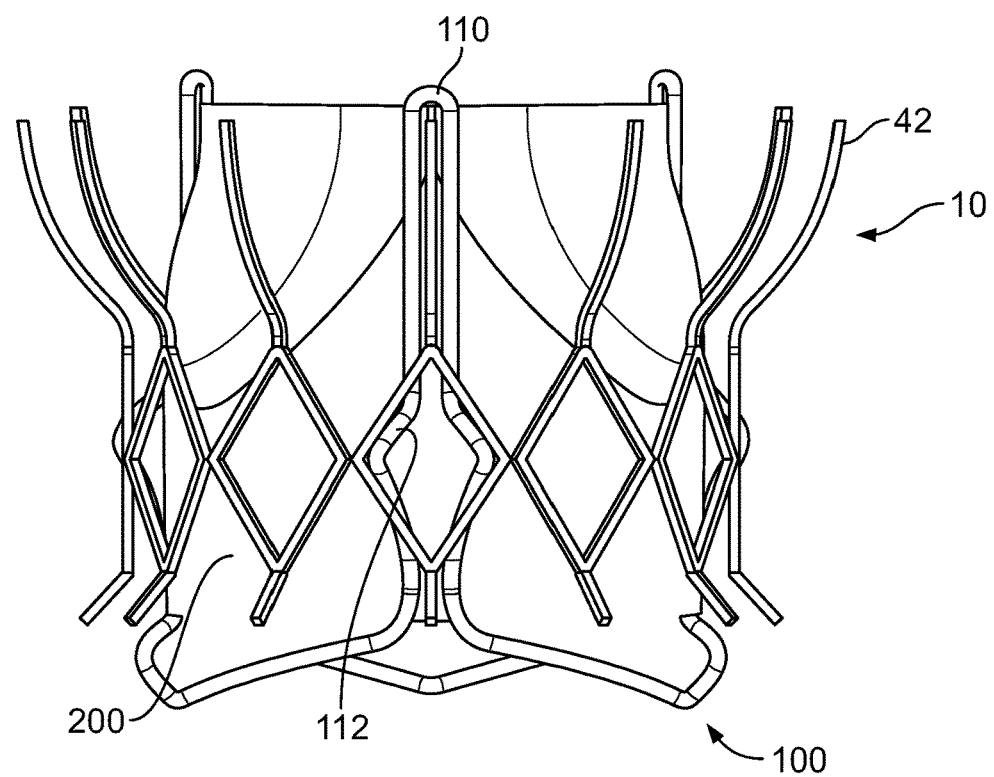
FIG. 12b is a simplified elevational view of the FIG. 12a structure.

FIGS. 12a-b are two views of illustrative embodiments of the assembly of components 10, 100, 200 when a short anchoring frame 10 like that shown in FIGS. 7a-c is used. FIG. 12b shows the use of spread-elbow projections 112. FIG. 12a shows the use of projections 112 that do not have the spread-elbow configuration. Thus elbows like 112 can point in the same direction (e.g., as in FIG. 12a) or in opposite directions (e.g., as in FIG. 12b).

Figure 13A:
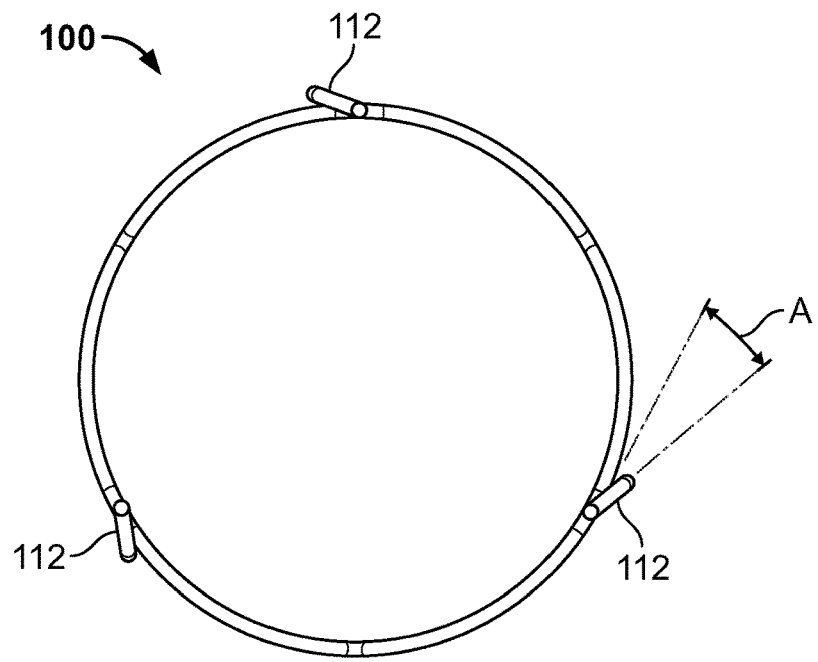
FIG. 13a is a simplified top view of another illustrative embodiment of a component in accordance with the invention.
Figure 13B:
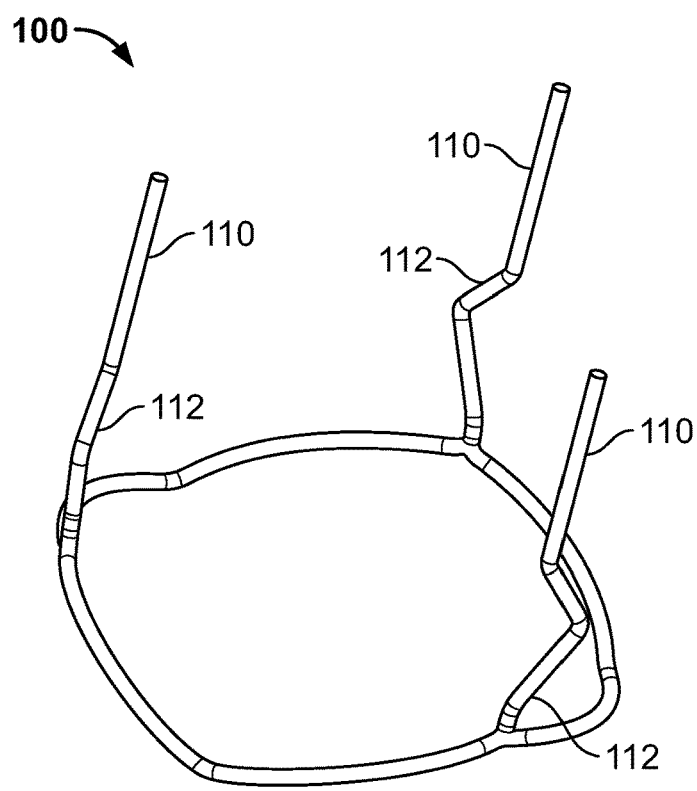
FIG. 13b is a simplified isometric or perspective view of the FIG. 13a structure.
Figure 13C:
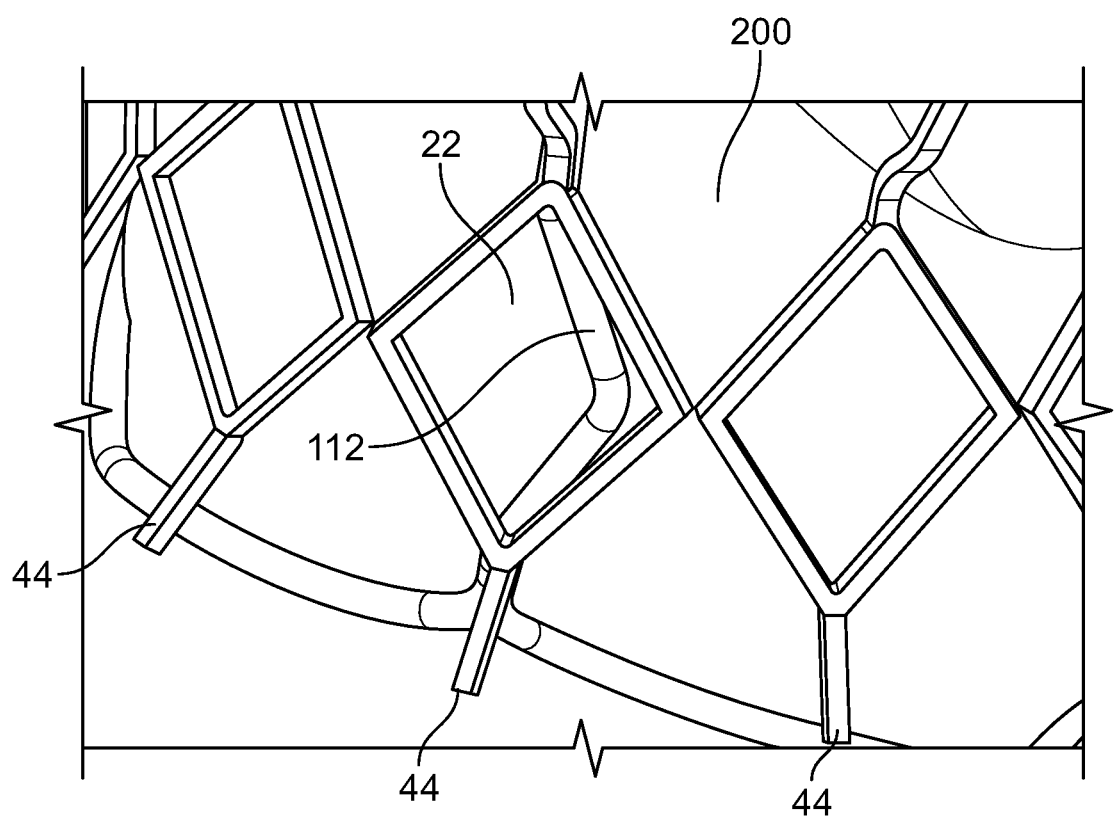
FIG. 13c is a simplified, partial, isometric or perspective view showing an illustrative use of the FIGS. 13a-b structure in accordance with the invention.

FIGS. 13a-c show a rotate and lock embodiment of a valve support structure 100 in accordance with the invention. In this embodiment each commissure post 110 is effectively a single member and includes a projection 112. As shown in FIG. 13a, projections 112 do not extend radially outwardly perpendicular to a circumference of the annular structure, but rather extend radially out at an angle A that is not a right angle to the circumference. FIG. 13c shows details of the interlocking engagement between angled projections 112 and cells 22 in structure 10. The valve support structure 100 is secured to anchoring structure 10 by using a rotate and lock feature. The valve frame 100 is inserted into the anchoring structure 10 and then rotated in the direction of the angled projections 112 to engage projections 112 with portions of the perimeter of cells 22.

Recapitulating and extending the foregoing, the following are some of the various possible features and highlights of the invention.

Two-stage deployment valve system. Valve frame 100 and anchoring frame 10 can be integrated into the same delivery system or can be accomplished using two separate delivery systems.

Lower profile of the integrated system. Especially lower profile if collapsible/expandable valve 100/200 and anchoring systems 10 are separate.

Anchoring/docking frame 10 is delivered and deployed first and independent of the valve 100/200.

The anchoring/docking frame 10 has anchoring features and mechanisms at the inflow edge 20, middle section 40, and the outflow edge 30 to secure it in place and prevent migration. The anchoring/docking frame 10 can also have anchoring sections at the inflow edge 20 only, middle section 40 only, outflow edge 30 only, or any combination thereof.

The anchoring frame 10 will anchor in place using native geometry (patient anatomy) and may remodel that geometry to provide an adequate landing site for the subsequently delivered valve 100/200.

The collapsed valve 100/200 is delivered second and deployed/expanded within the anchoring structure 10 upon reaching the landing site. The collapsed valve 100/200 can also be expanded just before reaching the anchoring frame 10 and then pushed in to lock.

The valve 100/200 has feature geometries (e.g., 112) to make it mate and interlock in place within the existing deployed anchoring structure 10.

The valve 100/200 has independently flexing commissure posts 110 that contribute to prolonged, durable performance by reducing stresses.

A cuff (e.g., like above-mentioned cuff 300) can be integrated onto the valve frame 100 assembly to aid in sealing in order to prevent perivalvular leaks. Alternatively or in addition, such a cuff 300 can be integrated onto the anchoring frame 10 for similar purposes as shown, for example, in FIG. 14 or 15.

The valve frame 100 remains in place via the interlocking mechanism 22/112, in addition to its radial force (frame 100 can be manufactured from memory-shaped nitinol or from stainless steel and then expanded with a balloon).

The slotted commissure post design (e.g., 110 in FIGS. 1a-b) facilitates leaflet integration by sliding the edges of the leaflets 200 in the inverted U-shaped opening in each post 110 and wrapping around before securing the leaflets to the valve frame 100. Alternatively, for this or other valve frames 100 shown herein, the valve frame may be dipped over specially designed mandrels to create polymeric leaflets that are integral with the frame. In other words, the leaflet structure may be created using a forming process producing polymeric leaflets that are integral with the valve support structure.

The symmetry of expanded frame cells 22 at the lower band (inflow side) 20 of the anchoring frame 10 allows freedom in valve radius orientation because the valve frame (stent) elbows 112 can interlock with any of the expanded cells 22.

In other embodiments, if rotational alignment between the valve 100/200 and the anchoring frame 10 is desired, a suture line (nitinol wire or any other appropriate member material) pre-attached to the valve 100/200 and running into corresponding and desired cell 22 locations in the anchoring frame can be used. The suture line can be used to guide the valve 100/200 as it is being advanced; and once at the desired location, the valve 100/200 can be deployed and the holding/retaining line can be removed. Upon deployment, the suture line can be cut and removed.

A sealing cuff (e.g., like 300) can be incorporated on the valve frame 100, the anchoring frame 10, or both, to prevent leakage.

Other interlocking concepts/geometries between the valve frame 100 and anchoring frame 10 are possible and can be employed. What has been presented is an example.

The contour/geometry of the interlocking cell 22 in the anchoring frame 10 can be of different geometries that would also adapt, mate, and interlock with corresponding shapes 112 on the valve frame 100.

The short anchoring frame embodiment (e.g., FIGS. 7a-c) has capabilities in anchoring using barbs 44 on the inflow end, using its outward bias radial force, and using elongated barbs 42 (straight or curved) on the outflow end. The elongated barbs 42 have a dual function (anchoring by engaging native calcified leaflets and holding those leaflets radially outwardly, away, and clear to prevent interference with new valve function). Another embodiment may have the barbs 42 connected together on the outflow end, allowing shorter sections to engage the native leaflets. The height of the short frame 10 can be short enough so it does not interfere with blood perfusion into the patient's coronary arteries.

The anchoring frame 10 can be self-expanding or balloon expandable. The valve frame 100 can also be self-expanding or balloon expandable.

The delivery system used in accordance with the invention can have both scenarios integrated in series or a desired combination of self- and balloon-expanding mechanisms.

The invention provides the ability to precisely size the valve frame 100 once the anchoring frame 10 is deployed (in the case of separate systems). Once the anchoring frame 10 is in place, the opening can be sized (measured, e.g., fluoroscopically) and the appropriate valve 100/200 size can be selected to be expanded and implanted within the anchoring frame 10.

Restating at least some of the foregoing in terms that may to some extent be different from terms used at other points in this specification, apparatus for use as a prosthetic heart valve may include an annular anchoring structure (e.g., 10) that is adapted for (1) delivery into a patient in a circumferentially collapsed condition, and (2) circumferential re-expansion and anchoring engagement with tissue of the patient when at an implant site in the patient. The apparatus may further include an annular valve support structure (e.g., 100) that is initially separate from the anchoring structure 10 and that is adapted for (1) delivery into the patient in a circumferentially collapsed condition, and (2) circumferential re-expansion and interengagement with the anchoring structure when adjacent to the anchoring structure in the patient. The apparatus may still further include a flexible leaflet structure (e.g., 200) disposed inside the valve support structure.

The above-mentioned anchoring structure 10 may include a plurality of closed-perimeter, open-center cells (e.g., 22) disposed in an array that extends annularly (circumferentially) around the anchoring structure.

The above-mentioned valve support structure 100 may include a plurality of projections (e.g., 112), each of which can extend radially outwardly into a respective one of the above-mentioned cells 22.

The above-mentioned valve support structure 100 may include a plurality of circumferentially spaced commissure post structures (e.g., 110). Each of the above-mentioned projections 112 may be on a respective one of the commissure post structures.

Each of the above-mentioned projections 112 may include first and second inclined surfaces (e.g., 113a and 113b in FIG. 4a) that meet at a radially outermost peak (e.g., 113c in FIG. 4a). The first inclined surface 113a may incline from the peak 113c radially inwardly in a direction toward an inflow end of the apparatus (e.g., toward the bottom as viewed in FIG. 4a). The second inclined surface 113b may incline from the peak 113c radially inwardly in a direction toward an outflow end of the apparatus (e.g., toward the top as viewed in FIG. 4a).

Each of the above-mentioned projections 112 and the respective cell 22 into which that projection can extend may be sized so that the first inclined surface 113a can contact a first portion (e.g., 23a in FIG. 6b) of the perimeter of the cell that is toward the inflow end of the apparatus, and also so that, at the same time, the second inclined surface 113b can contact a second portion (e.g., 23b in FIG. 6b) of the perimeter of the cell that is toward the outflow end of the apparatus. Interlocking features of this kind help prevent relative movement between frames 10 and 100 after those components have interlocked. (As used in contexts like this, "contact" may mean either direct contact or contact that is transmitted through one or more intervening layers of other material such as fabric, tissue, or the like.)

Each of the above-mentioned projections 112 may further include third and fourth inclined surfaces (e.g., 113d and 113e in FIG. 3a) that meet at a radially outermost peak (e.g., 113f in FIG. 3a). The third and fourth surfaces 113d and 113e and the second peak 113f may be circumferentially spaced from the first and second inclined surfaces 113a and 113b and the first peak 113c, respectively (e.g., as shown in FIG. 3a, or as shown in FIG. 5b). The third inclined surface 113d may incline from the second peak 113f radially inwardly in a direction toward the inflow end (e.g., toward the bottom in FIG. 3a), and the fourth inclined surface 113e may incline from the second peak 113f radially inwardly in a direction toward the outflow end (e.g., toward the top in FIG. 3a).

Each of the above-mentioned projections 112 and the respective cell 22 into which that projection can extend may be sized so that all four of the above-mentioned inclined surfaces 113a, 113b, 113d, and 113e can, at the same time, contact respective portions of the perimeter of the cell (see, for example, FIG. 10a where such four cell perimeter portions are identified as 25a, 25b, 25d and 25e). Two of these cell perimeter portions 25a and 25d are toward the inflow end (e.g., toward the bottom in FIG. 10a), and the other two cell perimeter portions 25b and 25e are toward the outflow end (e.g., toward the top in FIG. 10a).

In each of the above-mentioned projections 112, the first and third inclined surfaces 113a and 113d may diverge from one another toward the first and second peaks 113c and 113f (e.g., as shown in FIG. 3a). The same may be true of the second and fourth inclined surfaces 113d and 113e. This gives a projection 112 a spread elbow configuration as described elsewhere in this specification.

The above-mentioned first and third cell perimeter portions 25a and 25d may meet at a point (e.g., 27a in FIG. 10a) and may incline away from one another toward the outflow end (e.g., toward the top in FIG. 10a). The above-mentioned second and fourth cell perimeter portions 25b and 25e may similarly meet at a point (e.g., 27b in FIG. 10a) and may incline away from one another toward the inflow end (e.g., toward the bottom in FIG. 10a).

The above-mentioned anchoring structure 10 may include a plurality of members (e.g., 44 in FIG. 13c) that are adapted (e.g., as a result of resilient bias) to taper or incline radially outwardly at an oblique angle to the longitudinal axis of the anchoring structure on an inflow side of the patient's native heart valve annulus at the implant site. Alternatively or in addition, the anchoring structure 10 may include a plurality of members (e.g., 42) that are adapted (e.g., as a result of resilient bias) to taper or incline radially outwardly at an oblique angle to the longitudinal axis of the anchoring structure on an outflow side of the patient's native heart valve annulus at the implant site. In such a case, the members 42 may be adapted to push radially outwardly on the patient's native heart valve leaflets at the implant site.

The above-mentioned anchoring structure 10 may be resiliently biased to circumferentially re-expand. Alternatively or in addition, the above-mentioned valve support structure 100 may be resiliently biased to circumferentially re-expand.

The above-mentioned anchoring structure 10 may include an annular annulus inflow portion (e.g., 20) adapted for interengagement with the valve support structure 100. Anchoring structure 10 may further include an annular aortic outflow portion (e.g., 30) adapted for disposition in the patient's aorta downstream from the patient's native aortic valve at the implant site. Anchoring structure 10 may still further include at least one connecting strut (e.g., 42) extending between and connecting the annulus inflow portion 20 and the aortic outflow portion 30.

A method of implanting a prosthetic heart valve in a patient may include implanting an annular anchoring structure (e.g., 10) in the patient by delivering the anchoring structure into the patient in a circumferentially collapsed condition and then circumferentially expanding the anchoring structure while in the patient to implant the anchoring structure at an implant site in the patient. The method may further include delivering an annular valve support structure (e.g., 100), which is initially separate from the anchoring structure 10, into the patient in a circumferentially collapsed condition. The method may still further include circumferentially expanding the valve support structure 100 while in the patient, and interlocking the expanded valve support structure with the implanted anchoring structure 10.

A method like the above may employ inserting the valve support structure 100 into the implanted anchoring structure 10 in the direction that blood will flow through the implanted valve. Alternatively, the method may employ inserting the valve support structure 100 into the implanted anchoring structure 10 in a direction that is opposite to the above-mentioned bloodflow direction.

It will be understood that the foregoing is only illustrative of the principles of the invention, and that various modifications can be made by those skilled in the art without departing from the scope and spirit of the invention. For example, instead of both of components 10 and 100 being elastically compressible and re-expandable, either or both of those components may be plastically compressible and re-expandable. Such plastic re-expansion may be, for example, by inflation of a balloon catheter temporarily inserted inside the component to be plastically re-expanded.

The invention claimed is:

1. A prosthetic heart valve, comprising:
    a first frame having an expanded configuration and a collapsed configuration, the first frame in the expanded configuration having a longitudinal axis, an inflow end, an outflow end, a first portion adjacent the inflow end, and a second portion between the first portion and the outflow end, the first portion including a plurality of collapsible cells each having a perimeter and an open center, and the second portion including a plurality of struts spaced from one another in an annular direction of the first frame;
    a second frame having an expanded configuration and a collapsed configuration, the second frame having a plurality of circumferentially spaced commissure post structures and being adapted for (1) delivery into a patient separated from the first frame, and (2) engagement with the first frame in an assembled position in which the first frame is in the expanded configuration and the second frame is in the expanded configuration; and
    a valve assembly supported by the second frame.

2. The prosthetic heart valve as claimed in claim 1, wherein the second frame includes a plurality of projections, each projection extending radially outwardly into a respective one of the cells of the first frame in the assembled position.

3. The prosthetic heart valve as claimed in claim 2, wherein the first portion of the first frame tapers outwardly in a direction toward the inflow end in the expanded configuration.

4. The prosthetic heart valve as claimed in claim 3, wherein the second portion of the first frame bulges radially outwardly relative to the first portion of the first frame in the expanded configuration.

5. The prosthetic heart valve as claimed in claim 2, wherein each of the projections includes first and second inclined surfaces that meet at a radially outermost first peak, the first inclined surface in the assembled position inclining from the first peak radially inwardly in a direction toward the inflow end of the first frame, and the second inclined surface in the assembled position inclining from the first peak radially inwardly in a direction toward the outflow end of the first frame.

6. The prosthetic heart valve as claimed in claim 5, wherein each of the projections further includes third and fourth inclined surfaces that meet at a radially outermost second peak, the third and fourth inclined surfaces and the second peak being circumferentially spaced from the first and second inclined surfaces and the first peak, respectively, the third inclined surface in the assembled position inclining from the second peak radially inwardly in a direction toward the inflow end of the first frame, and the fourth inclined surface in the assembled position inclining from the second peak radially inwardly in a direction toward the outflow end of the first frame.

7. The prosthetic heart valve as claimed in claim 6, wherein, in each of the projections, the first and third inclined surfaces diverge from one another toward the first peak and the second peak, and the second and fourth inclined surfaces diverge from one another toward the first peak and the second peak.

8. The prosthetic heart valve as claimed in claim 1, wherein each of the struts extends from the first portion to a free end not connected to any structure.

9. The prosthetic heart valve as claimed in claim 8, wherein the second portion of the first frame is devoid of structure between annularly adjacent ones of the struts, whereby the annularly adjacent ones of the struts are not directly connected to one another.

10. The prosthetic heart valve as claimed in claim 1, wherein the valve assembly includes a plurality of leaflets.

11. The prosthetic heart valve as claimed in claim 10, further comprising a fabric cuff positioned around the outside of the first frame.

12. The prosthetic heart valve as claimed in claim 10, further comprising an annular cuff secured to at least one of the first frame or the second frame.

13. The prosthetic heart valve as claimed in claim 1, wherein the first frame includes a middle portion between the first portion and the second portion, the first portion in the expanded configuration having a first portion smallest circumference, the second portion in the expanded condition having a second portion smallest circumference that is not equal to the first portion smallest circumference, and the middle portion in the expanded configuration having a largest circumference that is larger than the first portion smallest circumference and the second portion smallest circumference.

14. The prosthetic heart valve as claimed in claim 13, wherein the first portion smallest circumference is less than the second portion smallest circumference.

15. The prosthetic heart valve as claimed in claim 1, wherein the plurality of cells are disposed in an array that extends annularly around the first frame.

16. The prosthetic heart valve as claimed in claim 1, wherein the second frame includes a plurality of projections and a plurality of circumferentially spaced commissure post structures, each of the projections being on a respective one of the commissure post structures.

* * * * *